(12) United States Patent
Brutnell et al.

(10) Patent No.: US 11,060,101 B2
(45) Date of Patent: Jul. 13, 2021

(54) COMPOSITIONS AND METHODS FOR INCREASING PLANT GROWTH AND YIELD

(71) Applicant: Benson Hill Biosystems, Inc., Research Triangle Park, NC (US)

(72) Inventors: Thomas P. Brutnell, St. Louis, MO (US); Benjamin N. Gray, Chapel Hill, NC (US); Todd C. Mockler, St. Louis, MO (US); Lin Wang, Grover, MO (US)

(73) Assignee: BENSON HILL, INC., St. Louis, MO (US)

( * ) Notice: Subject to any disclaimer, the term of this patent is extended or adjusted under 35 U.S.C. 154(b) by 0 days.

(21) Appl. No.: 15/324,501

(22) PCT Filed: Jul. 8, 2015

(86) PCT No.: PCT/US2015/039571
§ 371 (c)(1),
(2) Date: Jan. 6, 2017

(87) PCT Pub. No.: WO2016/007640
PCT Pub. Date: Jan. 14, 2016

(65) Prior Publication Data
US 2017/0198298 A1    Jul. 13, 2017

Related U.S. Application Data

(60) Provisional application No. 62/022,925, filed on Jul. 10, 2014.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8225* (2013.01); *C12N 15/8227* (2013.01); *C12N 15/8237* (2013.01); *C12N 15/8241* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 10,590,430 | B2 * | 3/2020 | Gray | C07K 14/195 |
| 2009/0183270 | A1 * | 7/2009 | Adams | C07K 14/4702 800/260 |
| 2009/0217414 | A1 * | 8/2009 | La Rosa | C07H 21/04 800/278 |
| 2010/0319089 | A1 * | 12/2010 | Azhakanandam | C12N 15/8241 800/294 |
| 2012/0227131 | A1 * | 9/2012 | Abad | C07K 14/4702 800/275 |
| 2013/0269061 | A1 * | 10/2013 | Lessard | A23K 10/12 800/284 |

FOREIGN PATENT DOCUMENTS

| | | |
|---|---|---|
| CN | 103773796 A | 5/2014 |
| WO | WO 00/28058 A2 | 5/2000 |
| WO | WO 2007/117693 A2 | 10/2007 |
| WO | WO 2010129501 A1 | 5/2010 |
| WO | WO 2012/162193 A2 | 11/2012 |

OTHER PUBLICATIONS

NCBI Reference Sequence: NM_001147802.1. published Apr. 10, 2009. pp. 1.*
NCBI Reference Sequence: NP_001141274.1. published Sep. 1, 2013. pp. 1-2.*
Yanez et al. An abiotic stress-responsive bZIP transcription factor from wild and cultivated tomatoes regulates stress-related genes. Plant Cell Reports. 2009. 28(10): 1497-1507.*
Hollung et al. Developmental, stress and ABA modulation of mRNA levels for bZip transcription factors and Vp1 in barley embryos and embryo-derived suspension cultures. Plant Molecular Biology. 1997. 35: 561-571.*
Shou et al. Expression of an active tobacco mitogen-activated protein kinase kinase kinase enhances freezing tolerance in transgneic maize. PNAS. 2004. 101(9): 3298-3303.*
Kasuga et al. A combination of the Arabidopsis DREB1A gene and stress-inducible rd29A promoter improved drought- and low-temperature stress tolerance in tobacco by gene transfer. Plant Cell Physiology. 2004. 45(3):346-350.*
Kessler et al. Plant responses to insect herbivory. The emerging molecular analysis. Annu. Rev. Plant Biology. 2002. 53: 299-328.*
Li et al. Expression analysis of genes encoding double B-boxzinc finger proteins in maize. Functional Integrated Genomics. 2017. 17:653-666.*
NCBI Reference Sequence: NM_001147802.1. published Sep. 1, 2013. pp. 1.*
Database Geneseq, "*Zea mays* B-box zinc finger protein BBX18," Seq: 206, 2013, 2 pages.
Database Geneseq, "*Oryza sativa*-B-box zinc finger protein," Seq: 220, 2013, 2 pages.
Database Geneseq, "Regulatory protein functional homolog sequence," Seq: 614, 2007, 2 pages.
Database Geneseq, "Regulatory protein functional homolog sequence," Seq: 616, 2007, 2 pages.

(Continued)

*Primary Examiner* — Ashley K Buran
(74) *Attorney, Agent, or Firm* — Womble Bond Dickinson (US) LLP

(57) ABSTRACT

Compositions and methods for improving plant growth are provided herein. Polynucleotides, polypeptides, and expression constructs for expressing transcription factors (TFs) whose expression may improve agronomic properties including but not limited to crop yield, biotic and abiotic stress tolerance, and early vigor, plants comprising the polynucleotides, polypeptides, and expression constructs, and methods of producing transgenic plants are also provided.

8 Claims, No Drawings
Specification includes a Sequence Listing.

(56) References Cited

OTHER PUBLICATIONS

Database Geneseq, "*Zeas mays* protein sequence," Seq: 806, 2009, 1 page.
Database Geneseq, "B. distachyon BBX18," Seq. 270, 2015, 2 pages.

* cited by examiner

SEQUENCE LISTING

```
<160> NUMBER OF SEQ ID NOS: 52

<210> SEQ ID NO 1
<211> LENGTH: 621
<212> TYPE: DNA
<213> ORGANISM: Zea mays
<220> FEATURE:
<221> NAME/KEY: misc_feature
<222> LOCATION: (1)...(641)
<223> OTHER INFORMATION: Gene Identifier: GRMZM2G143718

<400> SEQUENCE: 1
atgaggacca tctgcgacgt gtgcgagtcc gccccggccg tgctcttctg cgccgccgac      60
gaggccgccc tctgcaggcc gtgcgacgag aaggtgcaca tgtgcaacaa gctcgcctcc     120
aggcacgtga gggtgggcct cgccgacccg aacaagctcg tgaggtgcga catctgcgag     180
aactccccgg ccttcttcta ctgcgagatc gacggcacct ccctctgcct ctcctgcgac     240
```

```
atgaccgtgc acgtgggcgg caagaggacc cacggcaggt acctcctcct caggcagagg    300
gtggagttcc cgggcgacaa gccgggccac atggacgacg tgccgatgga gatccaggac    360
ccggagaacc agagggacca gaagaagccg ccgaaggagc agaccgccaa ccaccacaac    420
ggcgacgacc cggccaccga cggcaactgc gacgaccagg gcaacatcga ctccaagatg    480
atcgacctca acatgaggcc ggtgaggacc cacggccagg agtccaactc ccagacccag    540
ggcgtgggcc tctccgtgaa caaccacgac tccccgggcg tggtgccgac ctccaactcc    600
gagagggaca cctccaagtg a                                             621
```

```
<210> SEQ ID NO 2
<211> LENGTH: 206
<212> TYPE: PRT
<213> ORGANISM: Zea mays
<220> FEATURE:
<221> NAME/KEY: DOMAIN
<222> LOCATION: (1)...(206)
<223> OTHER INFORMATION: Gene Identifier: GRMZM2G143718

<400> SEQUENCE: 2
```

Met Arg Thr Ile Cys Asp Val Cys Glu Ser Ala Pro Ala Val Leu Phe
1               5                   10                  15

Cys Ala Ala Asp Glu Ala Ala Leu Cys Arg Pro Cys Asp Glu Lys Val
            20                  25                  30

His Met Cys Asn Lys Leu Ala Ser Arg His Val Arg Val Gly Leu Ala
        35                  40                  45

Asp Pro Asn Lys Leu Val Arg Cys Asp Ile Cys Glu Asn Ser Pro Ala
    50                  55                  60

Phe Phe Tyr Cys Glu Ile Asp Gly Thr Ser Leu Cys Leu Ser Cys Asp
65                  70                  75                  80

Met Thr Val His Val Gly Gly Lys Arg Thr His Gly Arg Tyr Leu Leu
                85                  90                  95

Leu Arg Gln Arg Val Glu Phe Pro Gly Asp Lys Pro Gly His Met Asp
            100                 105                 110

Asp Val Pro Met Glu Ile Gln Asp Pro Glu Asn Gln Arg Asp Gln Lys
        115                 120                 125

Lys Pro Pro Lys Glu Gln Thr Ala Asn His His Asn Gly Asp Asp Pro
    130                 135                 140

Ala Thr Asp Gly Asn Cys Asp Asp Gln Gly Asn Ile Asp Ser Lys Met
145                 150                 155                 160

Ile Asp Leu Asn Met Arg Pro Val Arg Thr His Gly Gln Glu Ser Asn
                165                 170                 175

Ser Gln Thr Gln Gly Val Gly Leu Ser Val Asn Asn His Asp Ser Pro
            180                 185                 190

Gly Val Val Pro Thr Ser Asn Ser Glu Arg Asp Thr Ser Lys
        195                 200                 205

```
<210> SEQ ID NO 3
<211> LENGTH: 258
<212> TYPE: DNA
<213> ORGANISM: Zea mays
<220> FEATURE:
<221> NAME/KEY: misc_feature
<222> LOCATION: (1)...(258)
<223> OTHER INFORMATION: Gene Identifier: GRMZM2G117497
```

<400> SEQUENCE: 3

```
atgtccgcct cacgcagctc ctctcccaac tccatctcac agtggagcca gaaagagaac      60
aagatgtttg aagaggcact cgcatactac ggcgagggca catccaaccg gtgggacaag     120
gtgtccagag ccatgggagg catcaagtct gctgaggagg tgcgctgcca ctatgaagat     180
cttgactatg acgtcaagat gattgaatca ggccacgtgc cgtaccccaa gtacaagaca     240
catggattct ggacctga                                                   258
```

<210> SEQ ID NO 4
<211> LENGTH: 85
<212> TYPE: PRT
<213> ORGANISM: Zea mays
<220> FEATURE:
<221> NAME/KEY: DOMAIN
<222> LOCATION: (1)...(85)
<223> OTHER INFORMATION: Gene Identifier: GRMZM2G117497

<400> SEQUENCE: 4

Met Ser Ala Ser Arg Ser Ser Ser Pro Asn Ser Ile Ser Gln Trp Ser
1               5                   10                  15

Gln Lys Glu Asn Lys Met Phe Glu Glu Ala Leu Ala Tyr Tyr Gly Glu
            20                  25                  30

Gly Thr Ser Asn Arg Trp Asp Lys Val Ser Arg Ala Met Gly Gly Ile
        35                  40                  45

Lys Ser Ala Glu Glu Val Arg Cys His Tyr Glu Asp Leu Asp Tyr Asp
    50                  55                  60

Val Lys Met Ile Glu Ser Gly His Val Pro Tyr Pro Lys Tyr Lys Thr
65                  70                  75                  80

His Gly Phe Trp Thr
                85

<210> SEQ ID NO 5
<211> LENGTH: 264
<212> TYPE: DNA
<213> ORGANISM: Zea mays
<220> FEATURE:
<221> NAME/KEY: misc_feature
<222> LOCATION: (1)...(264)
<223> OTHER INFORMATION: Gene Identifier: GRMZM2G158117

<400> SEQUENCE: 5

```
atgtctgcct cgcggagctc ctctcccaac tccatgtcac agtggagcca gaaagagaac      60
aagatgtttg aagaggcact cgcctactat ggcgagggca cacccaaccg gtgggacaag     120
gtgtccagcg ccatgggagg catcaagtct gccgaggagg tgcgctgcca ctatgaaaat     180
cttgattacg acgtcaagat gattgagtca ggcaatgtgc cgtaccccaa gtacaagaca     240
cagggattct ggacccgagg ttaa                                            264
```

<210> SEQ ID NO 6
<211> LENGTH: 87
<212> TYPE: PRT
<213> ORGANISM: Zea mays
<220> FEATURE:
<221> NAME/KEY: DOMAIN
<222> LOCATION: (1)...(87)
<223> OTHER INFORMATION: Gene Identifier: GRMZM2G158117

<400> SEQUENCE: 6

```
Met Ser Ala Ser Arg Ser Ser Pro Asn Ser Met Ser Gln Trp Ser
1               5                   10                  15

Gln Lys Glu Asn Lys Met Phe Glu Glu Ala Leu Ala Tyr Tyr Gly Glu
            20                  25                  30

Gly Thr Pro Asn Arg Trp Asp Lys Val Ser Ser Ala Met Gly Gly Ile
        35                  40                  45

Lys Ser Ala Glu Glu Val Arg Cys His Tyr Glu Asn Leu Asp Tyr Asp
50                  55                  60

Val Lys Met Ile Glu Ser Gly Asn Val Pro Tyr Pro Lys Tyr Lys Thr
65                  70                  75                  80

Gln Gly Phe Trp Thr Arg Gly
                85
```

<210> SEQ ID NO 7
<211> LENGTH: 282
<212> TYPE: DNA
<213> ORGANISM: Zea mays
<220> FEATURE:
<221> NAME/KEY: misc_feature
<222> LOCATION: (1)...(282)
<223> OTHER INFORMATION: Gene Identifier: GRMZM2G150260

<400> SEQUENCE: 7

```
atggcgtcta tgtcgctgag ctcgtcgagg gcgcagtgga cggcgaagca gaacaagctg      60
ttcgagcagg cgttggcggt gtacgacagg gacacgccgg accgctggca caacatcgcg     120
cgcgccgtgg gtggcaagtc ggcggacgag gtcaggcgct actacgagct gctggtgaag     180
gacttggagc acatcgaggc cggcaaggtg gccttccccg cgtacaggtg ccccggcggc     240
tacgacgacg ccgacagcga caggctgaag cacctgacct ga                       282
```

<210> SEQ ID NO 8
<211> LENGTH: 93
<212> TYPE: PRT
<213> ORGANISM: Zea mays
<220> FEATURE:
<221> NAME/KEY: DOMAIN
<222> LOCATION: (1)...(93)
<223> OTHER INFORMATION: Gene Identifier: GRMZM2G150260

<400> SEQUENCE: 8

```
Met Ala Ser Met Ser Leu Ser Ser Arg Ala Gln Trp Thr Ala Lys
1               5                   10                  15

Gln Asn Lys Leu Phe Glu Gln Ala Leu Ala Val Tyr Asp Arg Asp Thr
            20                  25                  30

Pro Asp Arg Trp His Asn Ile Ala Arg Ala Val Gly Gly Lys Ser Ala
        35                  40                  45

Asp Glu Val Arg Arg Tyr Tyr Glu Leu Leu Val Lys Asp Leu Glu His
50                  55                  60

Ile Glu Ala Gly Lys Val Ala Phe Pro Ala Tyr Arg Cys Pro Gly Gly
65                  70                  75                  80

Tyr Asp Asp Ala Asp Ser Asp Arg Leu Lys His Leu Thr
                85                  90
```

<210> SEQ ID NO 9
<211> LENGTH: 1689
<212> TYPE: DNA
<213> ORGANISM: Zea mays

```
<220> FEATURE:
<221> NAME/KEY: misc_feature
<222> LOCATION: (1)...(1689)
<223> OTHER INFORMATION: Gene Identifier: GRMZM2G165042

<400> SEQUENCE: 9
atgaaccagt tcgtccctga ttggagcaac atgggagaca cctccaggcc gctcggcgaa      60
gaagacgacc tcatcgagct gctatggtgc aacggccatg tcgtcatgca gagccagagc     120
caccggaagg tgccgccgag gccggagaag gcggcggcag tggcggctcc accagccccc     180
gcgtccgtgc cgcaggaaga cgagggcggc ctgtggttcc ccttcgcgct ggccgactcg     240
ctggacaagg acatcttctc ggagttcttc tgcgaggcac cgacgccggc accggcggcg     300
gcggatgcgg cgccggcggc ctctggtggt ggaaccggca ccgaagccgg cggcaagtcg     360
tgcggcgggg acgtcccagt cccagcagag acgacaggc gcggcggcgg cggggcgtgc      420
gcggtgtcgg cggggggaccc gtgcgacctg atgccgcctc ccaagtcgac gcccgcgtcc     480
tgctccaggc agcagacgac gatgagcctg gccaacggcg gcgacaatgc cggaggggac     540
ctgccgggcc tcgtccgtgc gggggcggag gccggcgcgt cgtcgatgct gagcgcgatc     600
gggtccagca tctgcgggag caaccaggtc ctggtgcagc gcgcggcgtg cgcgccgggg     660
cgcgcgtccg cgtccggctc cggaaccgcc cgcggcgacg gtccgggtc cgccgcgctg      720 ccgtcggcgg tgggcagcgc gaacgcgaac gccgtgggcg gcggcagggg ccacgaggcg     780
tcctcgtcgg ggcggtccaa ctactgctgc ttcggcgccg ccaccaccac aaccacaacc     840
accaccacgg agcccgcgag caccagcaac cggagcagca agcgcaagcg gctcgacacc     900
gaggactcgg agagtcccag cgaggacgcg gagtcggggt ccgccgcgat gttggcgcgc     960
aagccgccgc agaagatgac gacggcgcgg aggagccgcg ccgccgaagt gcacaacctg    1020
tcggagcgga ggagacgaga caggataaac gagaagatga gagccctgca agagctcata    1080
cctcactgca acaagacgga caaggcgtca atgcttgacg aggcgatcga gtacctcaag    1140
tcgctgcagc tgcaagtgca gatgatgtgg atgggcagcg ccggcatcgc ggcgccgccg    1200
gcggtgatgt tccccggcgt acaccagtac ctgcctcgga tgggcgtcgg gatgggcgcg    1260
gcagcggcgg cggcgctgcc gtccatgccg cggctgccgt tcatggcccc gcaaccggtg    1320
gtgcccagcg cgccggtgag cgtgggcccg gtgccggcct accggggcca catgcccgcg    1380
gtgggcatca cggagccgta cgggcactac atcggcgtca accacctgca gccggcgccg    1440
ccgccaccgc aggtccaggg cgtgagctac taccgccgc cgctggggc gacggcgaag     1500 gccgtgcagc aggctgcaga gcttcaccac gtgccgggc ccggcggcag catcatgccc     1560
gccggcgccg caccggagt gctgctcccg gagagcgcgc aaggcagagg gccaggtacg    1620
gtgccatgcg ctccgcccctt ctcatcctcc gcttcagttt ttgggctaca aatgggagca    1680
ctacgatga                                                            1689

<210> SEQ ID NO 10
<211> LENGTH: 562
<212> TYPE: PRT
<213> ORGANISM: Zea mays
<220> FEATURE:
<221> NAME/KEY: DOMAIN
<222> LOCATION: (1)...(562)
<223> OTHER INFORMATION: Gene Identifier: GRMZM2G165042
```

<400> SEQUENCE: 10

```
Met Asn Gln Phe Val Pro Asp Trp Ser Asn Met Gly Asp Thr Ser Arg
1               5                   10                  15

Pro Leu Gly Glu Glu Asp Asp Leu Ile Glu Leu Leu Trp Cys Asn Gly
            20                  25                  30

His Val Met Gln Ser Gln Ser His Arg Lys Val Pro Arg Pro
        35                  40                  45

Glu Lys Ala Ala Ala Val Ala Ala Pro Pro Ala Pro Ala Ser Val Pro
50                  55                  60

Gln Glu Asp Glu Gly Gly Leu Trp Phe Pro Phe Ala Leu Ala Asp Ser
65                  70                  75                  80

Leu Asp Lys Asp Ile Phe Ser Glu Phe Phe Cys Glu Ala Pro Thr Pro
                85                  90                  95

Ala Pro Ala Ala Ala Asp Ala Ala Pro Ala Ala Ser Gly Gly Gly Thr
                100                 105                 110

Gly Thr Glu Ala Gly Gly Lys Ser Cys Gly Gly Asp Val Pro Val Pro
            115                 120                 125

Ala Glu Asp Asp Arg Arg Gly Gly Gly Ala Cys Ala Val Ser Ala
            130                 135                 140

Gly Asp Pro Cys Asp Leu Met Pro Pro Pro Lys Ser Thr Pro Ala Ser
145                 150                 155                 160

Cys Ser Arg Gln Gln Thr Thr Met Ser Leu Ala Asn Gly Gly Asp Asn
                165                 170                 175

Ala Gly Gly Asp Leu Pro Gly Leu Val Arg Ala Gly Ala Glu Ala Gly
                180                 185                 190

Ala Ser Ser Met Leu Ser Ala Ile Gly Ser Ser Ile Cys Gly Ser Asn
            195                 200                 205

Gln Val Leu Val Gln Arg Ala Ala Cys Ala Pro Gly Arg Ala Ser Ala
    210                 215                 220

Ser Gly Ser Gly Thr Ala Arg Gly Asp Gly Ser Gly Ser Ala Ala Leu
225                 230                 235                 240

Pro Ser Ala Val Gly Ser Ala Asn Ala Asn Ala Val Gly Gly Gly Arg
                245                 250                 255

Gly His Glu Ala Ser Ser Ser Gly Arg Ser Asn Tyr Cys Cys Phe Gly
            260                 265                 270

Ala Ala Thr Thr Thr Thr Thr Thr Thr Thr Glu Pro Ala Ser Thr
            275                 280                 285

Ser Asn Arg Ser Ser Lys Arg Lys Arg Leu Asp Thr Glu Asp Ser Glu
    290                 295                 300

Ser Pro Ser Glu Asp Ala Glu Ser Gly Ser Ala Ala Met Leu Ala Arg
305                 310                 315                 320

Lys Pro Pro Gln Lys Met Thr Thr Ala Arg Arg Ser Arg Ala Ala Glu
                325                 330                 335

Val His Asn Leu Ser Glu Arg Arg Arg Asp Arg Ile Asn Glu Lys
            340                 345                 350

Met Arg Ala Leu Gln Glu Leu Ile Pro His Cys Asn Lys Thr Asp Lys
            355                 360                 365

Ala Ser Met Leu Asp Glu Ala Ile Glu Tyr Leu Lys Ser Leu Gln Leu
            370                 375                 380

Gln Val Gln Met Met Trp Met Gly Ser Ala Gly Ile Ala Ala Pro Pro
385                 390                 395                 400

Ala Val Met Phe Pro Gly Val His Gln Tyr Leu Pro Arg Met Gly Val
                405                 410                 415
```

```
Gly Met Gly Ala Ala Ala Ala Ala Leu Pro Ser Met Pro Arg Leu
            420                 425                 430
Pro Phe Met Ala Pro Gln Pro Val Val Pro Ser Ala Pro Val Ser Val
            435                 440                 445
Gly Pro Val Pro Ala Tyr Arg Gly His Met Pro Ala Val Gly Ile Thr
    450                 455                 460
Glu Pro Tyr Gly His Tyr Ile Gly Val Asn His Leu Gln Pro Ala Pro
465                 470                 475                 480
Pro Pro Pro Gln Val Gln Gly Val Ser Tyr Tyr Pro Pro Pro Leu Gly
                485                 490                 495
Ala Thr Ala Lys Ala Val Gln Gln Ala Ala Glu Leu His His Val Pro
            500                 505                 510
Gly Pro Gly Gly Ser Ile Met Pro Ala Gly Ala Ala Pro Gly Val Leu
            515                 520                 525
Leu Pro Glu Ser Ala Gln Gly Arg Gly Pro Gly Thr Val Pro Cys Ala
            530                 535                 540
Pro Pro Phe Ser Ser Ser Ala Ser Val Phe Gly Leu Gln Met Gly Ala
545                 550                 555                 560
Leu Arg

<210> SEQ ID NO 11
<211> LENGTH: 1299
<212> TYPE: DNA
<213> ORGANISM: Zea mays
<220> FEATURE:
<221> NAME/KEY: misc_feature
<222> LOCATION: (1)...(1299)
<223> OTHER INFORMATION: Gene Identifier: GRMZM2G162749

<400> SEQUENCE: 11
atgggggagg gcagagcagg agacggcctc atcaagctgt tcgggaagac catcccgtg      60 ccggagacgg ccgccgtcgg cgaggctgcc aaggacatgc aacaaagcgg cggcagcggc    120
agcggtacga ctgatccgaa agggcaagag aacaacgttc aggactccac aggctcgcct    180
ccgcagcagg aggtcgcgga caccgaagac tcgtcggcag acaaacagca gggcgaggcg    240 ggcaaccccaa aggagaagct caagaagccc gacaagatcc tgccgtgccc gcggtgcaac    300
agcatggaca ccaagttctg ctactacaac aactacaaca tcaaccagcc gcgccacttc    360
tgcaagaact gccagaggta ctggactgcc ggcggtgcca tgcgcaacgt gcccgtgggc    420
gcaggccggc gcaagagcaa gagcgcgtcg gccacttccc acttcctcca gagggtcagg    480
gccggtctgc ccgtcgaccc gctcgtctgc gcggcagcca agactaacgg cacggtgctc    540
agcttcggct ctgccatgtc cagcttagac ctcacggagc agatgaaaca gctcaaggaa    600
aagctcgtcc cgatagcggg ggacgagcgc tcagttgggt ctcgcactca aggaccttct    660
gccaaggcag aagacccgga ccggaaggag aatgttacag cagataaatc cgcgagagtt    720
gttcagcatc catgcatgac gaacggggtg ccatgtggc catttagctg tgcgccacca    780
gtaccggcct ctgcctgtta cggcccaggc agcatcgcaa tcccgttcta cccggcagca    840
gctgctgctg ctgcctactg ggttgcatg gttccaggag cttggagtgg cgcatggccg    900
cctcactccg gccagtccga gacgggctcg tccattacct ccgcctctcc agcagcatcc    960
accaagtcca acatctgctt cacgccagga aagcacccta gagaccgcga cgaggaagga   1020
ggcgccaaag gaaatggcaa ggtgtgggtg cccaagacga tccggatcga cgacgtggac   1080
gaggtggcca ggagctctat cctgtcgcta atcgggatcg gcggcgacaa ggcaggcaaa   1140
```

-continued

```
gatggcggca gaggctgcaa gctcgcaagg gttttgagc agaacgaaga ggcggcaagg     1200
acggcaactc ctcactcggc agccatcagc ggcttgccgt tcttgcaggg gaacccagct     1260
gcgctctcgc ggtcactgac cttccaggag gggtcttga                            1299
```

<210> SEQ ID NO 12
<211> LENGTH: 432
<212> TYPE: PRT
<213> ORGANISM: Zea mays
<220> FEATURE:
<221> NAME/KEY: DOMAIN
<222> LOCATION: (1)...(432)
<223> OTHER INFORMATION: Gene Identifier: GRMZM2G162749

<400> SEQUENCE: 12

```
Met Gly Glu Gly Arg Ala Gly Asp Gly Leu Ile Lys Leu Phe Gly Lys
1               5                   10                  15

Thr Ile Pro Val Pro Glu Thr Ala Ala Val Gly Glu Ala Ala Lys Asp
                20                  25                  30

Met Gln Gln Ser Gly Gly Ser Gly Thr Thr Asp Pro Lys Gly
        35                  40                  45

Gln Glu Asn Asn Val Gln Asp Ser Thr Gly Ser Pro Pro Gln Gln Glu
    50                  55                  60

Val Ala Asp Thr Glu Asp Ser Ser Ala Asp Lys Gln Gln Gly Glu Ala
65                  70                  75                  80

Gly Asn Pro Lys Glu Lys Leu Lys Lys Pro Asp Lys Ile Leu Pro Cys
                85                  90                  95

Pro Arg Cys Asn Ser Met Asp Thr Lys Phe Cys Tyr Tyr Asn Asn Tyr
                100                 105                 110

Asn Ile Asn Gln Pro Arg His Phe Cys Lys Asn Cys Gln Arg Tyr Trp
                115                 120                 125

Thr Ala Gly Gly Ala Met Arg Asn Val Pro Val Gly Ala Gly Arg Arg
    130                 135                 140

Lys Ser Lys Ser Ala Ser Ala Thr Ser His Phe Leu Gln Arg Val Arg
145                 150                 155                 160

Ala Gly Leu Pro Val Asp Pro Leu Val Cys Ala Ala Lys Thr Asn
                165                 170                 175

Gly Thr Val Leu Ser Phe Gly Ser Ala Met Ser Ser Leu Asp Leu Thr
                180                 185                 190

Glu Gln Met Lys Gln Leu Lys Glu Lys Leu Val Pro Ile Ala Gly Asp
                195                 200                 205

Glu Arg Ser Val Gly Ser Arg Thr Gln Gly Pro Ser Ala Lys Ala Glu
    210                 215                 220

Asp Pro Asp Arg Lys Glu Asn Val Thr Ala Asp Lys Ser Ala Arg Val
225                 230                 235                 240

Val Gln His Pro Cys Met Thr Asn Gly Val Ala Met Trp Pro Phe Ser
                245                 250                 255

Cys Ala Pro Pro Val Pro Ala Ser Ala Cys Tyr Gly Pro Gly Ser Ile
                260                 265                 270

Ala Ile Pro Phe Tyr Pro Ala Ala Ala Ala Ala Tyr Trp Gly
                275                 280                 285

Cys Met Val Pro Gly Ala Trp Ser Gly Ala Trp Pro Pro His Ser Gly
    290                 295                 300

Gln Ser Glu Thr Gly Ser Ser Ile Thr Ser Ala Ser Pro Ala Ala Ser
305                 310                 315                 320
```

Thr Lys Ser Asn Ile Cys Phe Thr Pro Gly Lys His Pro Arg Asp Arg
                325                 330                 335

Asp Glu Glu Gly Gly Ala Lys Gly Asn Gly Lys Val Trp Val Pro Lys
            340                 345                 350

Thr Ile Arg Ile Asp Asp Val Asp Glu Val Ala Arg Ser Ser Ile Leu
        355                 360                 365

Ser Leu Ile Gly Ile Gly Gly Asp Lys Ala Gly Lys Asp Gly Gly Arg
    370                 375                 380

Gly Cys Lys Leu Ala Arg Val Phe Glu Gln Asn Glu Glu Ala Ala Arg
385                 390                 395                 400

Thr Ala Thr Pro His Ser Ala Ala Ile Ser Gly Leu Pro Phe Leu Gln
                405                 410                 415

Gly Asn Pro Ala Ala Leu Ser Arg Ser Leu Thr Phe Gln Glu Gly Ser
            420                 425                 430

<210> SEQ ID NO 13
<211> LENGTH: 1083
<212> TYPE: DNA
<213> ORGANISM: Zea mays
<220> FEATURE:
<221> NAME/KEY: misc_feature
<222> LOCATION: (1)...(1083)
<223> OTHER INFORMATION: Gene Identifier: GRMZM2G134545

<400> SEQUENCE: 13
atggctggcg cggggggtgc gacggctgtg aagcagccgg cggcggggc gcccgacgct      60 ggggccagca ggagcggggt cggggctggc gccgccgggg cgccggtcgc cgacccgcgc    120
gccgaggcgc tgcggtgccc gcgctgcgac tcggccaaca ccaagttctg ctactacaac    180
aactactcgc tgtcgcagcc gcggcacttc tgcaaggcgt gcaagcgcta ctggacgcgc    240 ggggcacgc tccgcaacgt cccgtcggc ggggctgcc gcaagaacaa cgctccagg        300 agcagcggcg ggcccggcgc cggcgggagg aacgggtcct ccgctgctgc tgctgctgcc    360
gccgccgccg ccgccgtcac gtcctcctcg gcgccgtcga cgctgtccct cccgctgcat    420
acggggtccc tgccgtcgtt gtcctcggcg ctggggctgc ccggggggcgc ctcgctcgcg    480 tcgctcctcc tcgggaccgc tggctctggc ggtgaccacc tcggcctctt ccaggccgcc    540
atgcagtcgg tggtctcctc ggaggcgacc gcctacgaga tgcagcagca gcagcagacg    600
caggtggacc acctgctagg cctcggctac ggaggcgccg cgccggcgc cggcgcgcag    660 atccacctca gccgtggat gcacgaggca cccggtgctg gcgcgggcgg gatcatggac    720
agcttctacg cgccgctgct gtccagctcc ctcgtgccgg gctggagga gctgcacgtc    780 aaggcggagg tcgccggtgc cggggatcac cagcagaagc ccgcgcccgg ggaccagcag    840
agcgccagct gggagctgcc gacgccgtcg tcgtccaacg tcgacgccaa cgtcatcgca    900
tctgacgcgc tcatggccgc cgccgccgcg tccatgaacc ccggggttag ctccgccaca    960
gccgccacgg cgccaaccgt ccctcctcg ttcatgtact ggggcaacgg cggtattggc    1020
ggcgctgccg cggcgtggcc agacctcacc aactgcggat cctccattgc cacgttcttc    1080
tag                                                                  1083

<210> SEQ ID NO 14
<211> LENGTH: 360
<212> TYPE: PRT
<213> ORGANISM: Zea mays

```
<220> FEATURE:
<221> NAME/KEY: DOMAIN
<222> LOCATION: (1)...(360)
<223> OTHER INFORMATION: Gene Identifier: GRMZM2G134545

<400> SEQUENCE: 14
```

Met Ala Gly Ala Gly Ala Thr Ala Val Lys Gln Pro Ala Ala Gly
1               5                   10                  15

Ala Pro Asp Ala Gly Ala Ser Arg Ser Gly Val Gly Ala Gly Ala Ala
            20                  25                  30

Gly Ala Pro Val Ala Asp Pro Arg Ala Glu Ala Leu Arg Cys Pro Arg
            35                  40                  45

Cys Asp Ser Ala Asn Thr Lys Phe Cys Tyr Tyr Asn Asn Tyr Ser Leu
        50                  55                  60

Ser Gln Pro Arg His Phe Cys Lys Ala Cys Lys Arg Tyr Trp Thr Arg
65                  70                  75                  80

Gly Gly Thr Leu Arg Asn Val Pro Val Gly Gly Cys Arg Lys Asn
                    85                  90                  95

Lys Arg Ser Arg Ser Ser Gly Gly Pro Gly Ala Gly Gly Arg Asn Gly
                100                 105                 110

Ser Ser Ala Ala Ala Ala Ala Ala Ala Ala Ala Ala Val Thr Ser
                115                 120                 125

Ser Ser Ala Pro Ser Thr Leu Ser Leu Pro Leu His Thr Gly Ser Leu
                130                 135                 140

Pro Ser Leu Ser Ser Ala Leu Gly Leu Pro Gly Gly Ala Ser Leu Ala
145                 150                 155                 160

Ser Leu Leu Leu Gly Thr Ala Gly Ser Gly Gly Asp His Leu Gly Leu
                    165                 170                 175

Phe Gln Ala Ala Met Gln Ser Val Val Ser Ser Glu Ala Thr Ala Tyr
                180                 185                 190

Glu Met Gln Gln Gln Gln Gln Thr Gln Val Asp His Leu Leu Gly Leu
                195                 200                 205

Gly Tyr Gly Gly Ala Gly Ala Gly Ala Gly Ala Gln Ile His Leu Lys
                210                 215                 220

Pro Trp Met His Glu Ala Pro Gly Ala Gly Ala Gly Gly Ile Met Asp
225                 230                 235                 240

Ser Phe Tyr Ala Pro Leu Leu Ser Ser Ser Leu Val Pro Gly Leu Glu
                    245                 250                 255

Glu Leu His Val Lys Ala Glu Val Ala Gly Ala Gly Asp His Gln Gln
                260                 265                 270

Lys Pro Ala Pro Gly Asp Gln Gln Ser Ala Ser Trp Glu Leu Pro Thr
                275                 280                 285

Pro Ser Ser Ser Asn Val Asp Ala Asn Val Ile Ala Ser Asp Ala Leu
                290                 295                 300

Met Ala Ala Ala Ala Ser Met Asn Pro Gly Val Ser Ser Ala Thr
305                 310                 315                 320

Ala Ala Thr Ala Pro Thr Val Pro Ser Ser Phe Met Tyr Trp Gly Asn
                    325                 330                 335

Gly Gly Ile Gly Gly Ala Ala Ala Trp Pro Asp Leu Thr Asn Cys
                340                 345                 350

Gly Ser Ser Ile Ala Thr Phe Phe
                355                 360

```
<210> SEQ ID NO 15
<211> LENGTH: 747
<212> TYPE: DNA
<213> ORGANISM: Zea mays
<220> FEATURE:
<221> NAME/KEY: misc_feature
<222> LOCATION: (1)...(747)
<223> OTHER INFORMATION: Gene Identifier: GRMZM2G077147

<400> SEQUENCE: 15
atgtgcacga ggggccactg gaggccgtcg gaggacgaga agctgaaaga gctcgttgcg    60
ctgtacgggc cgcacaactg gaacgccatc gccgagaagc ttcaagggag atcagggaaa   120
agctgcaggc tgcggtggtt caaccagctg gacccgagga tcaaccggag ccccttctcg   180
gaggaggagg aggagctgct cctcgcctcc caccgcgtcc acggcaaccg ctgggccgtc   240
atcgccaggc tgttcccggg cgcaccgac aacgccgtca agaaccactg gcatgtgatc    300
atggcgcggc ggtgcaggga cggatgcgg ctgtcgaaca ggcgtgccgg cggcgctgct    360
gctgctggtg ctggtgccgt cgtcgtcgcc accggtgctg ctgccgaaga tggcagtaac   420
cctaggagcg ccaataagaa gccgaggcct gacgcgagcg gcatggcctc cttgctagac   480
aagtaccgaa gagaattttc cgccgtcccg tttgccatta accatgatag caatcagcag   540
cagggctatt gttcaaatac taacgaagac gcaaacaaat cagtcgaatt ctacgatttc   600
ctccaagtga acgcgaactc gagcgacacc aagtgtggtt cgagcattga ggagcaagag   660
gcggagagcc gggatgacga tcaagccgaa gggcaggtgc agttcataga tttcctggag   720
gttggggctt cccatcgccg ccggtga                                       747

<210> SEQ ID NO 16
<211> LENGTH: 248
<212> TYPE: PRT
<213> ORGANISM: Zea mays
<220> FEATURE:
<221> NAME/KEY: DOMAIN
<222> LOCATION: (1)...(248)
<223> OTHER INFORMATION: Gene Identifier: GRMZM2G077147

<400> SEQUENCE: 16

Met Cys Thr Arg Gly His Trp Arg Pro Ser Glu Asp Glu Lys Leu Lys
1               5                   10                  15

Glu Leu Val Ala Leu Tyr Gly Pro His Asn Trp Asn Ala Ile Ala Glu
            20                  25                  30

Lys Leu Gln Gly Arg Ser Gly Lys Ser Cys Arg Leu Arg Trp Phe Asn
        35                  40                  45

Gln Leu Asp Pro Arg Ile Asn Arg Ser Pro Phe Ser Glu Glu Glu Glu
    50                  55                  60

Glu Leu Leu Leu Ala Ser His Arg Val His Gly Asn Arg Trp Ala Val
65                  70                  75                  80

Ile Ala Arg Leu Phe Pro Gly Arg Thr Asp Asn Ala Val Lys Asn His
                85                  90                  95

Trp His Val Ile Met Ala Arg Arg Cys Arg Glu Arg Met Arg Leu Ser
            100                 105                 110

Asn Arg Arg Ala Gly Gly Ala Ala Ala Gly Ala Gly Ala Val Val
        115                 120                 125

Val Ala Thr Gly Ala Ala Ala Glu Asp Gly Ser Asn Pro Arg Ser Ala
    130                 135                 140

Asn Lys Lys Pro Arg Pro Asp Ala Ser Gly Met Ala Ser Leu Leu Asp
145                 150                 155                 160
```

```
Lys Tyr Arg Arg Glu Phe Ser Ala Val Pro Phe Ala Ile Asn His Asp
            165                 170                 175

Ser Asn Gln Gln Gln Gly Tyr Cys Ser Asn Thr Asn Glu Asp Ala Asn
        180                 185                 190

Lys Ser Val Glu Phe Tyr Asp Phe Leu Gln Val Asn Ala Asn Ser Ser
    195                 200                 205

Asp Thr Lys Cys Gly Ser Ser Ile Glu Glu Gln Glu Ala Glu Ser Arg
210                 215                 220

Asp Asp Asp Gln Ala Glu Gly Gln Val Gln Phe Ile Asp Phe Leu Glu
225                 230                 235                 240

Val Gly Ala Ser His Arg Arg Arg
            245
```

<210> SEQ ID NO 17
<211> LENGTH: 1634
<212> TYPE: DNA
<213> ORGANISM: Zea mays
<220> FEATURE:
<221> NAME/KEY: misc_feature
<222> LOCATION: (1)...(1634)
<223> OTHER INFORMATION: PepC promoter and 5'UTR

<400> SEQUENCE: 17

```
gggggggggg gggggagggt cgtcgtctcc ctatctgacc tctcttctgc attggattgc      60
ctttttcggt actctattta aaacttaaaa gtacaaatga ggtgccggat tgatggagtg     120
atatataagt ttgatgtgtt tttcacataa gtgacaagta ttattgaaag agaacatttg     180
cattgctact gtttgcatat gggaaaattg agaattgtat catgccatgg ccgatcagtt     240
ctttacttag ctcgatgtaa tgcacaatgt tgatagtatg tcgaggatct agcgatgtaa     300
tggtgttagg acacgtggtt agctactaat ataaatgtaa ggtcattcga tggtttttct     360
attttcaatt acctagcatt atctcatttc taattgtgat aacaaatgca ttagaccata     420
attctgtaaa tatgtacatt taagcacaca gtctatattt taaaattctt cttttttgtgt    480
ggatatccca acccaaatcc acctctctct tcaatccgtg catgttcacc gctgccaagt     540
gccaacaaca catcgcatcg tgcatatctt tgttggcttg tgcacggtcg cgccaatgg      600
aggagacacc tgtacggtgc ccttggtaga acaacatcct tatccctata tgtatggtgc     660
ccttcgtaga atgacacccc ttatccctac aatagccatg tatgcatacc aagaattaaa     720
tatactttt  cttgaaccac aataatttat tatagcggca cttcttgttc aggttgaaca     780
cttatttgga acaataaaat gccgagttcc taaccacagg ttcacttttt tttttcctta    840
tcctcctagg aaactaaatt ttaaaatcat aaatttaatt taaatgttaa tggaaacaaa     900
aaattatcta caaagacgac tcttagccac agccgcctca ctgcaccctc aaccacatcc     960
tgcaaacaga caccctcgcc acatccctcc agattcttca ctccgatgca gcctacttgc    1020
taacagacgc cctctccaca tcctgcaaag cattcctcca aattcttgcg atcccccgaa    1080
tccagcatta actgctaagg gacgccctct ccacatcctg ctacccaatt agccaacgga    1140
ataacacaag aaggcaggtg agcagtgaca agcacgtca  acagcaccga gccaagccaa    1200
aaaggagcaa ggaggagcaa gcccaagccg cagccgcagc tctccaggtc cccttgcgat    1260
tgccgccagc agtagcagac acccctctcc acatcccctc cggccgctaa cagcagcaag    1320
ccaagccaaa aaggagcctc agccgcagcc ggttccgttg cggttaccgc cgatcacatg    1380
cccaaggccg cgccttttccg aacgccgagg gccgcccgtt cccgtgcaca gccacacaca    1440
cacccgcccg ccaacgactc cccatcccta tttgaaccca cccgcgcact gcattgatca    1500
```

| | |
|---|---|
| acaaaaagca gccattgggg atttgctttg aaaagtggac acctgcggat gacaccaatc | 1560 |
| gcatcgcagc agcacgagca gcacgccgtg ccgctccaac catctcgctt ccgtgcttag | 1620 |
| cttcccgccg cgcc | 1634 |

<210> SEQ ID NO 18
<211> LENGTH: 1814
<212> TYPE: DNA
<213> ORGANISM: Zea mays
<220> FEATURE:
<221> NAME/KEY: misc_feature
<222> LOCATION: (1)...(1814)
<223> OTHER INFORMATION: CA1 promoter and 5'UTR

<400> SEQUENCE: 18

| | |
|---|---|
| ccccgcccat gtcagcaggc ctccgaggct tttggttgcc caaccagccc atgggctgaa | 60 |
| ttcataacag tgttggcaca cagtttcctc ttcactcgga agcttattat tatcgatcct | 120 |
| gaaccagaga ctagcagagc tagcatttcg acgacgcgtc tcaactctca acctccaagt | 180 |
| ccacctcgtg tacgtgctgc cttgccagtt gccactgggc actgctggcc cagtgaccaa | 240 |
| ccatgcgtta gatctgacag caccaccgaa ccatcctccc cggtgatcaa caaacgacgg | 300 |
| cagccacatc ttgcacccaa cgtgatgatg aatgatgcct agaacttttg acaacaaaac | 360 |
| gcagcacagg tagcaggttt aattcaacaa gactttctac tatatagagc cacaccatag | 420 |
| agataactaa tctgtgcgca aagccaaagt gctgacggca actgtggtgc agccttttca | 480 |
| tctccgtttt taagtttttt gcccctcctt ttgttttctg tttttctggg aactctttaa | 540 |
| accgccgtgg cgccgtgtaa actttgctgt agccttttcg cgtgcaatgg cagagcgccc | 600 |
| tgttcttttc ctgctaaaga aaaaaaaaa ggagcacctg atcgctggca ggcccacggc | 660 |
| ccacccaact gtgtctgtaa cgctcggcgt ccctgcattg catgccaagt gccaaccacc | 720 |
| agtccatagc agggtcaggg agaccgcaga tgaggccggg gcaacggtga tgccgcaaag | 780 |
| aggattcaga atccttttc ttttcttttc tttaccacc gggctggcat cacagattac | 840 |
| acgcgcagta gagtaagcac gtctctctcg tagccaagaa caacagtcta cacagctcgc | 900 |
| tttctccgcc cttgtctggg cgttacggca ggcaagcccc ctcgttttct tctgctcgcg | 960 |
| ttctccttcc atgtccacat ctcctgtgcc accgcacgca aggtgccaac gctccctcgc | 1020 |
| cgcagtagca tcgcgtccac acaaactgca cctccactag atacggcggt gatccggcga | 1080 |
| gagagcgcga cacgcacagg ccagctagcg tttctccgac gccgcgcgtt tcatcatttc | 1140 |
| ccgcttcccc tgcccccggc cgcgcgcgcg cgcccgtgtg gtccagacca ggacgcgcgc | 1200 |
| ggatgtgcat ccggcgcgcg cccgtcggcc acacggtgcc gccgcgcgtt atcccgagcc | 1260 |
| ctgtcctgtc ctgtcctgtt ccatctcgcg cgcgaggggg ggagggagg gcagcgagtg | 1320 |
| gcgcgctggc ggatgaggcg ccgagtggcc cgcatccacc ggcgcaggcg agccgcacga | 1380 |
| cgccgccgcg ctcgcggacc gccgccgcca cacatgcgca cccccggccc gcggggctgt | 1440 |
| aacggccttg tcgccacgcg tgcgccccgt gtgtataagg aggcagcgcg tacagggggc | 1500 |
| gacaacgata agcggcactc gcacgatcaa tgtacacatt gcccgtccgc gccaccacat | 1560 |
| ccagcatcgt cgccagcctc gccaccccg cgccgtcctc ctcctccggc tccggctccg | 1620 |
| gccgcccag gccaggctc atccggaacg ccccccgtctt cgccgccccc gccaccgtcg | 1680 |
| tgtaaacggg acgcgggca gctgaggagt caaacgagag agatcgagag aaagaaaggg | 1740 |
| agggcatcca ccagccgccg gcgataagag gggaggagag agaggccaga gaagaggagg | 1800 |
| agaagaagaa gaaa | 1814 |

```
<210> SEQ ID NO 19
<211> LENGTH: 737
<212> TYPE: DNA
<213> ORGANISM: Artificial Sequence
<220> FEATURE:
<221> NAME/KEY: misc_feature
<222> LOCATION: (1)...(737)
<223> OTHER INFORMATION: 4xRGCGR promoter and maize CA1 5'UTR
<220> FEATURE:
<223> OTHER INFORMATION: Sorghum bicolor (promoter) and Zea mays (5'UTR)

<400> SEQUENCE: 19
gaagcgagtg gcgcgctggc ggatgaggcg gcgagtggcc cggatgcacc ggcgcaggcg      60
agcgaagcga gtggcgcgct ggcggatgag gcggcgagtg gcccggatgc accggcgcag     120
gcgagcgaag cgagtggcgc gctggcggat gaggcggcga gtggcccgga tgcaccggcg     180
caggcgagcg aagcgagtgg cgcgctggcg gatgaggcgg cgagtggccc ggatgcaccg     240
gcgcaggcga gccgcacgcc gccgcccgcc gcggcgctcg cgcgcggacc gctgccgcct     300
gccgccacac aatgcgagcg cgcgcgcaca cacacacaca ccacccgggc ggggggggctg     360 tagtagtaac ggccttgtct tgtcggcacg cgcgcgtccg tgtgtataag gaggcaggcc     420
cgcgacaacg ataagcggca ctcgcacgat caatgtacac attgcccgtc cgcgccacca     480
catccagcat cgtcgccagc ctcgccaccc ccgcgccgtc ctcctcctcc ggctccggct     540
ccggccgccc caggcccagg ctcatccgga acgcccccgt cttcgccgcc ccgccaccg     600 tcgtgtaaac gggacggcgg gcagctgagg agtcaaacga gagagatcga gagaaagaaa     660
gggagggcat ccaccagccg ccggcgataa gaggggagga gagagaggcc agagaagagg     720
aggagaagaa gaagaaa                                                    737

<210> SEQ ID NO 20
<211> LENGTH: 258
<212> TYPE: DNA
<213> ORGANISM: Oryza sativa
<220> FEATURE:
<221> NAME/KEY: misc_feature
<222> LOCATION: (1)...(258)
<223> OTHER INFORMATION: Gene Identifier: LOC_Os05g49240

<400> SEQUENCE: 20
atgtctgggt cccggagctc ctcccccaac tcgaagtctg agtggagcag gaaggagaac      60
aagatgttcg aggaggcgct cgcctactac ggcgaggaca cgcccaaccg gtgggacaag     120
gtggccagcg ccatgggagg catcaagtcc gctgaggaga tccgctgcca ctacgaagac     180
ctcaccgatg acgtcaagac gatcgagtcc gggcgagtgc agttccccaa gtacaagacg     240
cagggatact ggacctga                                                   258

<210> SEQ ID NO 21
<211> LENGTH: 85
<212> TYPE: PRT
<213> ORGANISM: Oryza sativa
<220> FEATURE:
<221> NAME/KEY: DOMAIN
<222> LOCATION: (1)...(85)
<223> OTHER INFORMATION: Gene Identifier: LOC_Os05g49240

<400> SEQUENCE: 21

Met Ser Gly Ser Arg Ser Ser Ser Pro Asn Ser Lys Ser Glu Trp Ser
1               5                   10                  15

Arg Lys Glu Asn Lys Met Phe Glu Glu Ala Leu Ala Tyr Tyr Gly Glu
            20                  25                  30
```

Asp Thr Pro Asn Arg Trp Asp Lys Val Ala Ser Ala Met Gly Gly Ile
            35                  40                  45

Lys Ser Ala Glu Glu Ile Arg Cys His Tyr Asp Leu Thr Asp Asp
 50                  55                  60

Val Lys Thr Ile Glu Ser Gly Arg Val Gln Phe Pro Lys Tyr Lys Thr
 65                  70                  75                  80

Gln Gly Tyr Trp Thr
                85

<210> SEQ ID NO 22
<211> LENGTH: 636
<212> TYPE: DNA
<213> ORGANISM: Oryza sativa
<220> FEATURE:
<221> NAME/KEY: misc_feature
<222> LOCATION: (1)...(636)
<223> OTHER INFORMATION: Gene Identifier: LOC_Os09g35880

<400> SEQUENCE: 22
atgcggacga tctgcgacgt gtgcgagagc gcgccggcgg tgctcttctg cgtggccgac      60
gaggccgcgc tctgccggtc ctgcgacgag aaggtgcata tgtgtaacaa gcttgctagg     120
cggcacgtga gagttgggct tgcagaccct aataaagttc aacgctgtga tatatgtgaa     180 aatgccccg ccttcttcta ttgcgagata gatggtacat cactttgcct tagttgtgat     240
atgactgttc atgttggtgg gaaacgaacc catggaagat acctgctcct aaggcaacgg     300
gttgaatttc caggagataa accaggtcat atggatgatg ttgctatgca acagaaagat     360
cctgaaaacc ggacggatca aagaaggcc cctcactcag taacaaagga gcaaatggca     420
aaccatcata atgtgtctga tgatccagcc tcagatggca actgcgatga ccagggtaac     480
atcgattcca aaatgattga tcttaatatg agacccgtcc gtactcatgg acaaggttca     540
aactcacaga ctcagggcgt ggatgttagc gtcaacaatc atgattctcc aggagtggtg     600
ccaacatgta atttcgaacg agaagccaac aaataa                                636

<210> SEQ ID NO 23
<211> LENGTH: 211
<212> TYPE: PRT
<213> ORGANISM: Oryza sativa
<220> FEATURE:
<221> NAME/KEY: DOMAIN
<222> LOCATION: (10)...(211)
<223> OTHER INFORMATION: Gene Identifier: LOC_Os09g35880

<400> SEQUENCE: 23

Met Arg Thr Ile Cys Asp Val Cys Glu Ser Ala Pro Ala Val Leu Phe
 1               5                  10                  15

Cys Val Ala Asp Glu Ala Ala Leu Cys Arg Ser Cys Asp Glu Lys Val
                20                  25                  30

His Met Cys Asn Lys Leu Ala Arg Arg His Val Arg Val Gly Leu Ala
            35                  40                  45

Asp Pro Asn Lys Val Gln Arg Cys Asp Ile Cys Glu Asn Ala Pro Ala
 50                  55                  60

Phe Phe Tyr Cys Glu Ile Asp Gly Thr Ser Leu Cys Leu Ser Cys Asp
 65                  70                  75                  80

Met Thr Val His Val Gly Gly Lys Arg Thr His Gly Arg Tyr Leu Leu
                85                  90                  95

Leu Arg Gln Arg Val Glu Phe Pro Gly Asp Lys Pro Gly His Met Asp
                100                 105                 110

```
Asp Val Ala Met Gln Gln Lys Asp Pro Glu Asn Arg Thr Asp Gln Lys
            115                 120                 125

Lys Ala Pro His Ser Val Thr Lys Glu Gln Met Ala Asn His His Asn
    130                 135                 140

Val Ser Asp Asp Pro Ala Ser Asp Gly Asn Cys Asp Asp Gln Gly Asn
145                 150                 155                 160

Ile Asp Ser Lys Met Ile Asp Leu Asn Met Arg Pro Val Arg Thr His
                165                 170                 175

Gly Gln Gly Ser Asn Ser Gln Thr Gln Gly Val Asp Val Ser Val Asn
            180                 185                 190

Asn His Asp Ser Pro Gly Val Val Pro Thr Cys Asn Phe Glu Arg Glu
            195                 200                 205

Ala Asn Lys
    210

<210> SEQ ID NO 24
<211> LENGTH: 258
<212> TYPE: DNA
<213> ORGANISM: Oryza sativa
<220> FEATURE:
<221> NAME/KEY: misc_feature
<222> LOCATION: (1)...(258)
<223> OTHER INFORMATION: Gene Identifier: LOC_Os05g49240

<400> SEQUENCE: 24
atgtctgggt cccggagctc ctcccccaac tcgaagtctg agtggagcag gaaggagaac      60
aagatgttcg aggaggcgct cgcctactac ggcgaggaca cgcccaaccg gtgggacaag     120
gtggccagcg ccatgggagg catcaagtcc gctgaggaga tccgctgcca ctacgaagac     180
ctcaccgatg acgtcaagac gatcgagtcc gggcgagtgc agttccccaa gtacaagacg     240
cagggatact ggacctga                                                    258

<210> SEQ ID NO 25
<211> LENGTH: 85
<212> TYPE: PRT
<213> ORGANISM: Oryza sativa
<220> FEATURE:
<221> NAME/KEY: DOMAIN
<222> LOCATION: (1)...(85)
<223> OTHER INFORMATION: Gene Identifier: LOC_Os05g49240

<400> SEQUENCE: 25

Met Ser Gly Ser Arg Ser Ser Pro Asn Ser Lys Ser Glu Trp Ser
1               5                   10                  15

Arg Lys Glu Asn Lys Met Phe Glu Glu Ala Leu Ala Tyr Tyr Gly Glu
            20                  25                  30

Asp Thr Pro Asn Arg Trp Asp Lys Val Ala Ser Ala Met Gly Gly Ile
        35                  40                  45

Lys Ser Ala Glu Glu Ile Arg Cys His Tyr Glu Asp Leu Thr Asp Asp
    50                  55                  60

Val Lys Thr Ile Glu Ser Gly Arg Val Gln Phe Pro Lys Tyr Lys Thr
65                  70                  75                  80

Gln Gly Tyr Trp Thr
            85

<210> SEQ ID NO 26
<211> LENGTH: 327
<212> TYPE: DNA
<213> ORGANISM: Oryza sativa
```

```
<220> FEATURE:
<221> NAME/KEY: misc_feature
<222> LOCATION: (1)...(327)
<223> OTHER INFORMATION: Gene Identifier: LOC_Os01g44390

<400> SEQUENCE: 26
atggcgtcga tgtcggtgag ctcgtcgagg gcgccgcagt ggacggcgag gcagaacgag      60
cagttcgagc gggcgctggc ggtgtacgac agggacacgc cggagcggtg cacaacatc     120 gcgcgcgccg ttgcggggaa gtccgccgac gaggtgaagc tctactacga cctgctcgtg    180
gaggacgtca agcgcatcga gaccgggaag gtgcccttcc ccgcgtacag gtgccccag    240 cccgcgattg caggtcagtg catcggaaag aaggccaccg cgcgcggccg cttaatttcg   300
atcgtgttgt tcaccggagt ttactaa                                         327

<210> SEQ ID NO 27
<211> LENGTH: 108
<212> TYPE: PRT
<213> ORGANISM: Oryza sativa
<220> FEATURE:
<221> NAME/KEY: DOMAIN
<222> LOCATION: (1)...(108)
<223> OTHER INFORMATION: Gene Identifier: LOC_Os01g44390

<400> SEQUENCE: 27

Met Ala Ser Met Ser Val Ser Ser Ser Arg Ala Pro Gln Trp Thr Ala
1               5                   10                  15

Arg Gln Asn Glu Gln Phe Glu Arg Ala Leu Ala Val Tyr Asp Arg Asp
                20                  25                  30

Thr Pro Glu Arg Trp His Asn Ile Ala Arg Ala Val Ala Gly Lys Ser
            35                  40                  45

Ala Asp Glu Val Lys Leu Tyr Tyr Asp Leu Leu Val Glu Asp Val Lys
        50                  55                  60

Arg Ile Glu Thr Gly Lys Val Pro Phe Pro Ala Tyr Arg Cys Pro Gln
65                  70                  75                  80

Pro Ala Ile Ala Gly Gln Cys Ile Gly Lys Lys Ala Thr Ala Arg Gly
                85                  90                  95

Arg Leu Ile Ser Ile Val Leu Phe Thr Gly Val Tyr
                100                 105

<210> SEQ ID NO 28
<211> LENGTH: 1485
<212> TYPE: DNA
<213> ORGANISM: Oryza sativa
<220> FEATURE:
<221> NAME/KEY: misc_feature
<222> LOCATION: (1)...(1485)
<223> OTHER INFORMATION: Gene Identifier: LOC_Os03g43810

<400> SEQUENCE: 28
atgaaccagt tcgtccctga ttggagcaac atgggtgacg catccaggac actcggcgaa      60
gatgacaacc tcattgagct gctctggtgc aacggccatg tcgtcatgca gagccagaat     120
caccaccgga agctgccgcc gaggccgccg gagaaggcgg cggcggcggc ggtgcaagaa    180
gacgaggccg gctgtggtt cccgttcgcg ctcgccgact cgctggagaa ggacatcttc     240
tcggacctct tctacgaggc gcccgtcgcg gcgacggcgg aggcggcgcc tgctggcccg   300
ggcgcgggcg ccgacggcga aggaaagact tgcaagggcg acgcggcaat ggcggaggag   360
gagcgtggcg gccgggcgc ggcgtccgag gcgccgcgcg agctgatgcc gccgcccaag    420
tcgacgaacg cgtcctgctc gaggcagcag acgatgagcc tggcggacgg cggcgacaac   480
```

-continued

```
gccggggacc tgtcggagct cgtccggcg aggaggtcgt ccggcggcgc ggctcggcgg      540
aaggcggagg ccggcggcgg cggcggcggc gcgtcgtcgt cgatgctgag cgcgatcggg      600
tcgagcatct gcgggagcaa ccaggtgcag gtgcagcagc gcacggcgag cgagcccggg      660
cgccgcggcg cgccgccctc ggcggtgggg agcgcgaacg ccatcccctg cggcgggcgc      720
gaccacggcc acggccacga ggcgaccacc gtggcgtcgt cgtcggggcg gtccaactgc      780
tgcttcggca ccaccaccac cacggagccg acgagcacca gcaaccggag cagcaagcgc      840
aagcggctcg acaccaccga ggactccgag agccccagcg aggacgcgga gtcggagtcg      900
gcggcgctgg cgcgcaagcc gccggcgaag atgacgacgg cgcggaggag ccgcgccgcc      960
gaggtgcaca acctctccga ggaggagga cgggacagga tcaacgagaa gatgagagcc     1020
ctgcaggagc tcataccaca ctgcaacaag actgacaagg cgtcgatgct ggacgaggcg     1080
atcgagtacc tcaagtctct gcagctgcag ctgcagatga tgtggatggg gagcgggatg     1140
gcgccgccgg tgatgttccc gggggtgcac cagtatctgc cgaggatggg cgtcgggatg     1200
ggggcggcgg cggcggcgat gccgaggatg ccgttcatgg cggcgccgca gccggtggtg     1260
cccacaccgc cggtgaacca ccttgacctg ggcgtcaacc acctgcagcc gccgccgacc     1320
cagggagtgg ggtattatcc gttggggcc aaggccgtgc agcagcagca aaatccacca     1380
cttcacgtgc caaatggaag cattatgcct cctcctgaaa atgcacccaa cacaggatca     1440
ggtatgggat ccttctactt ctacttctac ttctcttccg attaa                    1485
```

<210> SEQ ID NO 29
<211> LENGTH: 494
<212> TYPE: PRT
<213> ORGANISM: Oryza sativa
<220> FEATURE:
<221> NAME/KEY: DOMAIN
<222> LOCATION: (1)...(494)
<223> OTHER INFORMATION: Gene Identifier: LOC_Os03g43810

<400> SEQUENCE: 29

```
Met Asn Gln Phe Val Pro Asp Trp Ser Asn Met Gly Asp Ala Ser Arg
1               5                   10                  15

Thr Leu Gly Glu Asp Asp Asn Leu Ile Glu Leu Leu Trp Cys Asn Gly
            20                  25                  30

His Val Met Gln Ser Gln Asn His His Arg Lys Leu Pro Pro Arg
        35                  40                  45

Pro Pro Glu Lys Ala Ala Ala Ala Val Gln Glu Asp Glu Ala Gly
    50                  55                  60

Leu Trp Phe Pro Phe Ala Leu Ala Asp Ser Leu Glu Lys Asp Ile Phe
65                  70                  75                  80

Ser Asp Leu Phe Tyr Glu Ala Pro Val Ala Ala Thr Ala Glu Ala Ala
                85                  90                  95

Pro Ala Gly Pro Gly Ala Gly Ala Asp Gly Glu Gly Lys Thr Cys Lys
            100                 105                 110

Gly Asp Ala Ala Met Ala Glu Glu Glu Arg Gly Gly Pro Gly Ala Ala
        115                 120                 125

Ser Glu Ala Pro Arg Glu Leu Met Pro Pro Lys Ser Thr Asn Ala
    130                 135                 140

Ser Cys Ser Arg Gln Gln Thr Met Ser Leu Ala Asp Gly Gly Asp Asn
145                 150                 155                 160

Ala Gly Asp Leu Ser Glu Leu Val Arg Ala Arg Arg Ser Ser Gly Gly
                165                 170                 175
```

| Ala | Ala | Arg | Arg | Lys | Ala | Glu | Ala | Gly | Gly | Gly | Gly | Gly | Ala | Ser |
|     |     |     | 180 |     |     |     | 185 |     |     |     |     | 190 |     |     |

| Ser | Ser | Met | Leu | Ser | Ala | Ile | Gly | Ser | Ser | Ile | Cys | Gly | Ser | Asn | Gln |
|     | 195 |     |     |     |     | 200 |     |     |     |     | 205 |     |     |     |     |

| Val | Gln | Val | Gln | Gln | Arg | Thr | Ala | Ser | Glu | Pro | Gly | Arg | Arg | Gly | Ala |
|     | 210 |     |     |     |     | 215 |     |     |     |     | 220 |     |     |     |     |

| Pro | Pro | Ser | Ala | Val | Gly | Ser | Ala | Asn | Ala | Ile | Pro | Cys | Gly | Gly | Arg |
| 225 |     |     |     |     | 230 |     |     |     |     | 235 |     |     |     |     | 240 |

| Asp | His | Gly | His | Gly | His | Glu | Ala | Thr | Thr | Val | Ala | Ser | Ser | Ser | Gly |
|     |     |     |     | 245 |     |     |     |     | 250 |     |     |     |     | 255 |     |

| Arg | Ser | Asn | Cys | Cys | Phe | Gly | Thr | Thr | Thr | Thr | Glu | Pro | Thr | Ser |
|     |     |     | 260 |     |     |     |     | 265 |     |     |     |     | 270 |     |

| Thr | Ser | Asn | Arg | Ser | Ser | Lys | Arg | Lys | Arg | Leu | Asp | Thr | Thr | Glu | Asp |
|     | 275 |     |     |     |     | 280 |     |     |     |     | 285 |     |     |     |     |

| Ser | Glu | Ser | Pro | Ser | Glu | Asp | Ala | Glu | Ser | Glu | Ser | Ala | Ala | Leu | Ala |
|     | 290 |     |     |     |     | 295 |     |     |     |     | 300 |     |     |     |     |

| Arg | Lys | Pro | Pro | Ala | Lys | Met | Thr | Thr | Ala | Arg | Arg | Ser | Arg | Ala | Ala |
| 305 |     |     |     |     | 310 |     |     |     |     | 315 |     |     |     |     | 320 |

| Glu | Val | His | Asn | Leu | Ser | Glu | Arg | Arg | Arg | Asp | Arg | Ile | Asn | Glu |
|     |     |     |     | 325 |     |     |     |     | 330 |     |     |     |     | 335 |

| Lys | Met | Arg | Ala | Leu | Gln | Glu | Leu | Ile | Pro | His | Cys | Asn | Lys | Thr | Asp |
|     |     |     | 340 |     |     |     |     | 345 |     |     |     |     | 350 |     |     |

| Lys | Ala | Ser | Met | Leu | Asp | Glu | Ala | Ile | Glu | Tyr | Leu | Lys | Ser | Leu | Gln |
|     | 355 |     |     |     |     | 360 |     |     |     |     | 365 |     |     |     |     |

| Leu | Gln | Leu | Gln | Met | Met | Trp | Met | Gly | Ser | Gly | Met | Ala | Pro | Pro | Val |
|     | 370 |     |     |     |     | 375 |     |     |     |     | 380 |     |     |     |     |

| Met | Phe | Pro | Gly | Val | His | Gln | Tyr | Leu | Pro | Arg | Met | Gly | Val | Gly | Met |
| 385 |     |     |     |     | 390 |     |     |     |     | 395 |     |     |     |     | 400 |

| Gly | Ala | Ala | Ala | Ala | Ala | Met | Pro | Arg | Met | Pro | Phe | Met | Ala | Ala | Pro |
|     |     |     |     | 405 |     |     |     |     | 410 |     |     |     |     | 415 |     |

| Gln | Pro | Val | Val | Pro | Thr | Pro | Pro | Val | Asn | His | Leu | Asp | Leu | Gly | Val |
|     |     |     | 420 |     |     |     |     | 425 |     |     |     |     | 430 |     |     |

| Asn | His | Leu | Gln | Pro | Pro | Thr | Gln | Gly | Val | Gly | Tyr | Tyr | Pro | Leu |
|     |     | 435 |     |     |     |     | 440 |     |     |     |     | 445 |     |     |

| Gly | Ala | Lys | Ala | Val | Gln | Gln | Gln | Asn | Pro | Pro | Leu | His | Val | Pro |
|     | 450 |     |     |     |     | 455 |     |     |     |     | 460 |     |     |     |

| Asn | Gly | Ser | Ile | Met | Pro | Pro | Glu | Asn | Ala | Pro | Asn | Thr | Gly | Ser |
| 465 |     |     |     |     | 470 |     |     |     |     | 475 |     |     |     | 480 |

| Gly | Met | Gly | Ser | Phe | Tyr | Phe | Tyr | Phe | Tyr | Phe | Ser | Ser | Asp |
|     |     |     |     | 485 |     |     |     |     | 490 |     |     |     |     |

<210> SEQ ID NO 30
<211> LENGTH: 1323
<212> TYPE: DNA
<213> ORGANISM: Oryza sativa
<220> FEATURE:
<221> NAME/KEY: misc_feature
<222> LOCATION: (1)...(1323)
<223> OTHER INFORMATION: Gene Identifier: LOC_Os03g07360

<400> SEQUENCE: 30

```
atgggggagt gcaaggtggg aggaggaggc ggaggcggag actgcttgat caagctgttc      60
gggaagacca tccccgtgcc agagcccggc gcctgcgccg ccggcgatgt tgataaggac     120
cttcaacaca gtggcagcag cacgactgaa ccgaaaactc aagagaacac cgttcaagac     180
tccacaagtc cacctccgca gccagaggtc gtcgacaccg aggactcttc agctgataag     240
```

```
aactcatcag agaatcagca gcagcagggc gatacggcca accagaagga gaagctgaag      300
aagcctgaca agatcctgcc gtgccccogg tgtagcagca tggacaccaa gttctgctac      360
tacaacaact acaacatcaa ccagccgcgc cacttctgca agaactgcca gaggtactgg      420
acagcgggtg gtgccatgcg caacgtgcct gtgggtgcag ccgacgcaa gagcaagagc       480 gtatcggccg cttcccattt cctccagagg gtcagggctg ctctgcccgg tgatcctcct      540
ctctatgccc cagtgaagac taatggcacc gttctcagct tcggctccga cctgtccacc      600
ttagacctca cagaacaaat gaagcatcta aaagataagt ttatcccaac aaccggtatc      660
aagaacaccg acgagatgcc agtcggtttg tgtgctgaag gattgtcgaa acagaagaa       720 tcgaaccaaa cgaacctaaa ggagaaagtt tcagcagata gatctccaaa tgttgcacaa      780
cacccatgca tgaacggagg agccatgtgg ccatttggcg tggcaccacc acctgcttat      840
tacacttcaa gcattgcaat tccattctat ccagctgcag cagctgctgt tgctgcatac      900
tggggctgca tggttccagg agcttggaac gctccatggc caccgcagtc ccaatcccaa      960
tcggtttcat catcaagtgc tgcttctcca gtatccacaa tgaccaactg cttcagatta     1020
ggaaagcacc ctagagatgg tgatgaggaa ctggatagca agggtaatgg caaggtgtgg     1080
gtgccgaaga cggttcggat cgacgatgtc gacgaggtgg ccaggagctc tatctggtcg     1140
cttattggga tcaagggtga caaggtggga gcagatcatg gcagaggatg caagcttgca     1200 aaggttttg agtcaaagga tgaggcaaag gcatcaactc acacagcgat cagcagcttg      1260
ccattcatgc aggggaaccc ggctgcccta acacgctcgg tgaccttcca agagggatct     1320
tga                                                                    1323
```

<210> SEQ ID NO 31
<211> LENGTH: 440
<212> TYPE: PRT
<213> ORGANISM: Oryza sativa
<220> FEATURE:
<221> NAME/KEY: DOMAIN
<222> LOCATION: (1)...(440)
<223> OTHER INFORMATION: Gene Identifier: LOC_Os03g07360

<400> SEQUENCE: 31

```
Met Gly Glu Cys Lys Val Gly Gly Gly Gly Gly Asp Cys Leu
1               5                   10                  15

Ile Lys Leu Phe Gly Lys Thr Ile Pro Val Pro Glu Pro Gly Ala Cys
            20                  25                  30

Ala Ala Gly Asp Val Asp Lys Asp Leu Gln His Ser Gly Ser Ser Thr
        35                  40                  45

Thr Glu Pro Lys Thr Gln Glu Asn Thr Val Gln Asp Ser Thr Ser Pro
    50                  55                  60

Pro Pro Gln Pro Glu Val Val Asp Thr Glu Ser Ser Ala Asp Lys
65                  70                  75                  80

Asn Ser Ser Glu Asn Gln Gln Gln Gly Asp Thr Ala Asn Gln Lys
                85                  90                  95

Glu Lys Leu Lys Lys Pro Asp Lys Ile Leu Pro Cys Pro Arg Cys Ser
            100                 105                 110

Ser Met Asp Thr Lys Phe Cys Tyr Tyr Asn Asn Tyr Asn Ile Asn Gln
        115                 120                 125

Pro Arg His Phe Cys Lys Asn Cys Gln Arg Tyr Trp Thr Ala Gly Gly
    130                 135                 140

Ala Met Arg Asn Val Pro Val Gly Ala Gly Arg Arg Lys Ser Lys Ser
145                 150                 155                 160
```

Val Ser Ala Ala Ser His Phe Leu Gln Arg Val Arg Ala Ala Leu Pro
                165                 170                 175

Gly Asp Pro Pro Leu Tyr Ala Pro Val Lys Thr Asn Gly Thr Val Leu
            180                 185                 190

Ser Phe Gly Ser Asp Leu Ser Thr Leu Asp Leu Thr Glu Gln Met Lys
        195                 200                 205

His Leu Lys Asp Lys Phe Ile Pro Thr Thr Gly Ile Lys Asn Thr Asp
    210                 215                 220

Glu Met Pro Val Gly Leu Cys Ala Glu Gly Leu Ser Lys Thr Glu Glu
225                 230                 235                 240

Ser Asn Gln Thr Asn Leu Lys Glu Lys Val Ser Ala Asp Arg Ser Pro
                245                 250                 255

Asn Val Ala Gln His Pro Cys Met Asn Gly Ala Met Trp Pro Phe
            260                 265                 270

Gly Val Ala Pro Pro Ala Tyr Tyr Thr Ser Ser Ile Ala Ile Pro
        275                 280                 285

Phe Tyr Pro Ala Ala Ala Ala Val Ala Ala Tyr Trp Gly Cys Met
    290                 295                 300

Val Pro Gly Ala Trp Asn Ala Pro Trp Pro Gln Ser Gln Ser Gln
305                 310                 315                 320

Ser Val Ser Ser Ser Ser Ala Ala Ser Pro Val Ser Thr Met Thr Asn
                325                 330                 335

Cys Phe Arg Leu Gly Lys His Pro Arg Asp Gly Asp Glu Glu Leu Asp
            340                 345                 350

Ser Lys Gly Asn Gly Lys Val Trp Val Pro Lys Thr Val Arg Ile Asp
        355                 360                 365

Asp Val Asp Glu Val Ala Arg Ser Ser Ile Trp Ser Leu Ile Gly Ile
    370                 375                 380

Lys Gly Asp Lys Val Gly Ala Asp His Gly Arg Gly Cys Lys Leu Ala
385                 390                 395                 400

Lys Val Phe Glu Ser Lys Asp Glu Ala Lys Ala Ser Thr His Thr Ala
                405                 410                 415

Ile Ser Ser Leu Pro Phe Met Gln Gly Asn Pro Ala Ala Leu Thr Arg
            420                 425                 430

Ser Val Thr Phe Gln Glu Gly Ser
        435                 440

<210> SEQ ID NO 32
<211> LENGTH: 1080
<212> TYPE: DNA
<213> ORGANISM: Oryza sativa
<220> FEATURE:
<221> NAME/KEY: misc_feature
<222> LOCATION: (1)...(1080)
<223> OTHER INFORMATION: Gene Identifier: LOC_Os07g32510

<400> SEQUENCE: 32
atggctggag cgggggtgc ggctacggct gcagcgggag aggaggtgg gggaggggtg      60 gcggcgggga ggagtggagg tggtggtggt ggtggcgcgg cggcggcggc ggggcgggg    120 gcgccggacc cgagggcgga ggcgctgcgg tgcccgcggt gcgactcggc gaacaccaag    180
ttctgctact acaacaacta ctcgctgtcg cagccgcggc acttctgcaa ggcgtgcaag    240
cgctactgga cgcgcggcgg cacgctgcgg aacgtccccg tcggcggcgg gtgccggaag    300
aacaagcggt cgaggagcgg cggcgcggcg cctggtggcg cgtggggag gggcgggcct    360 ggaggcgggg cggcggcggc cgtctcgtcg gctggcggcg gtgcagctgg gacttcgccc    420

-continued

```
gcgtcgtcgc tggcgctgcc gcagccaggg tcgctgccgt cgctgtcgtc ggcgctgggg    480
ctcaccgggg gaacctcgct ggcgtcgctg ctgctcggga gcggcggctc cgggggtgac    540
cacctcgggc tcttccaggc catgcagtcg gtggtgtccg acgcggccgc gttcgagatg    600
caccagcagc atcagtcgca ggtggatcac ctgctcggcc tcggctacgg cgccgcgggg    660
gcgcagatcc aggcggccaa gccgtggctg catgacggcg gcgccaccgg tggcctcctc    720
gacggcttct acgcgccgct cctgtccggc tccatcgtgc cggggctcga ggagctccaa    780
gtcaaggcgg aggccaccac cggcgaccac cagcagaagt catcggcggc ggcggccggt    840
gagcagagct gggacctgcc gacgccgtcg tcgtccaacg tcgaggcgag catcatcgcg    900
tcggacgcgc tcatggccgc cgcggccgcg tcgatgaacc cggcggtcag cgccgccgcc    960
gcctccacgg cgccgtccgc gcagtcgctc ctctactggg gcaacggcgg cattggcgcc   1020
gccgccgcgg catggccgga cctcgccaac tgcggatcct ccatagcgac gctcttctag   1080
```

<210> SEQ ID NO 33
<211> LENGTH: 359
<212> TYPE: PRT
<213> ORGANISM: Oryza sativa
<220> FEATURE:
<221> NAME/KEY: DOMAIN
<222> LOCATION: (1)...(359)
<223> OTHER INFORMATION: Gene Identifier: LOC_Os07g32510

<400> SEQUENCE: 33

```
Met Ala Gly Ala Gly Gly Ala Ala Thr Ala Ala Ala Gly Gly Gly Gly
1               5                   10                  15

Gly Gly Gly Val Ala Ala Gly Arg Ser Gly Gly Gly Gly Gly Gly Gly
                20                  25                  30

Ala Ala Ala Ala Ala Gly Ala Gly Ala Pro Asp Pro Arg Ala Glu Ala
            35                  40                  45

Leu Arg Cys Pro Arg Cys Asp Ser Ala Asn Thr Lys Phe Cys Tyr Tyr
        50                  55                  60

Asn Asn Tyr Ser Leu Ser Gln Pro Arg His Phe Cys Lys Ala Cys Lys
65                  70                  75                  80

Arg Tyr Trp Thr Arg Gly Gly Thr Leu Arg Asn Val Pro Val Gly Gly
                85                  90                  95

Gly Cys Arg Lys Asn Lys Arg Ser Arg Ser Gly Gly Ala Ala Pro Gly
                100                 105                 110

Gly Gly Val Gly Arg Gly Gly Pro Gly Gly Gly Ala Ala Ala Ala Val
            115                 120                 125

Ser Ser Ala Gly Gly Gly Ala Ala Gly Thr Ser Pro Ala Ser Ser Leu
130                 135                 140

Ala Leu Pro Gln Pro Gly Ser Leu Pro Ser Leu Ser Ser Ala Leu Gly
145                 150                 155                 160

Leu Thr Gly Gly Thr Ser Leu Ala Ser Leu Leu Gly Ser Gly Gly
                165                 170                 175

Ser Gly Gly Asp His Leu Gly Leu Phe Gln Ala Met Gln Ser Val Val
            180                 185                 190

Ser Asp Ala Ala Ala Phe Glu Met His Gln Gln His Gln Ser Gln Val
        195                 200                 205

Asp His Leu Leu Gly Leu Gly Tyr Gly Ala Ala Gly Ala Gln Ile Gln
    210                 215                 220

Ala Ala Lys Pro Trp Leu His Asp Gly Gly Ala Thr Gly Gly Leu Leu
225                 230                 235                 240
```

Asp Gly Phe Tyr Ala Pro Leu Leu Ser Gly Ser Ile Val Pro Gly Leu
            245                 250                 255

Glu Glu Leu Gln Val Lys Ala Glu Ala Thr Thr Gly Asp His Gln Gln
        260                 265                 270

Lys Ser Ser Ala Ala Ala Ala Gly Glu Gln Ser Trp Asp Leu Pro Thr
    275                 280                 285

Pro Ser Ser Ser Asn Val Glu Ala Ser Ile Ile Ala Ser Asp Ala Leu
290                 295                 300

Met Ala Ala Ala Ala Ser Met Asn Pro Ala Val Ser Ala Ala Ala
305                 310                 315                 320

Ala Ser Thr Ala Pro Ser Ala Gln Ser Leu Leu Tyr Trp Gly Asn Gly
            325                 330                 335

Gly Ile Gly Ala Ala Ala Ala Trp Pro Asp Leu Ala Asn Cys Gly
        340                 345                 350

Ser Ser Ile Ala Thr Leu Phe
        355

<210> SEQ ID NO 34
<211> LENGTH: 738
<212> TYPE: DNA
<213> ORGANISM: Oryza sativa
<220> FEATURE:
<221> NAME/KEY: misc_feature
<222> LOCATION: (1)...(738)
<223> OTHER INFORMATION: Gene Identifier: LOC_Os03g51110

<400> SEQUENCE: 34
atgtgcacca ggggccactg gaggccgtcg gaggacgaga agctgaagga gctcgtcgcg      60
cggtacgggc cgcataactg gaacgccata gccgagaagc tccaagggcg atcaggcaaa     120
agctgcaggc ttaggtggtt caaccagctc gacccaagaa tcaaccggag ccccttcacc     180
gaggaggagg aggagctcct cctcgcgtcg caccgcgccc acggcaaccg gtgggcggtg     240
atcgcgaggc tcttcccggg ccgcacggac aacgccgtca gaaccactg gcatgtgatc     300 atggcgcggc ggtgcaggga gcggatgcgg ctgtcgaatc gccggggcgg cgccgccgcc     360
gccggtgctg cgaaaggcga cgagagccca gctaggatta gcaacggcga aagacggcg     420 acgaggcctc ctgccacgaa tggcagcggc atggccatgg cctccttgct cgacaagtac     480
cgaagagaat gcggcgccgc tggcctgttt gcaattggca gacaccataa cagcaaggag     540
gattattgtt catctactaa tgaagatacg agtaaatcgg tggagtttta cgacttcctc     600
caggtgaatg cgagctcgag cgacaccaag tgcggctcga gcattgagga gcaagaggat     660
aaccgggatg atgatcaagc tgaagggcag gtgcagctca tagatttcat ggaggttggg     720
actacttctc gtcaatga                                                   738

<210> SEQ ID NO 35
<211> LENGTH: 245
<212> TYPE: PRT
<213> ORGANISM: Oryza sativa
<220> FEATURE:
<221> NAME/KEY: DOMAIN
<222> LOCATION: (1)...(245)
<223> OTHER INFORMATION: Gene Identifier: LOC_Os03g51110

<400> SEQUENCE: 35

Met Cys Thr Arg Gly His Trp Arg Pro Ser Glu Asp Glu Lys Leu Lys
1               5                   10                  15

Glu Leu Val Ala Arg Tyr Gly Pro His Asn Trp Asn Ala Ile Ala Glu
            20                  25                  30

Lys Leu Gln Gly Arg Ser Gly Lys Ser Cys Arg Leu Arg Trp Phe Asn
            35                  40                  45

Gln Leu Asp Pro Arg Ile Asn Arg Ser Pro Phe Thr Glu Glu Glu
    50                  55                  60

Glu Leu Leu Leu Ala Ser His Arg Ala His Gly Asn Arg Trp Ala Val
65                  70                  75                  80

Ile Ala Arg Leu Phe Pro Gly Arg Thr Asp Asn Ala Val Lys Asn His
                85                  90                  95

Trp His Val Ile Met Ala Arg Arg Cys Arg Glu Arg Met Arg Leu Ser
                100                 105                 110

Asn Arg Arg Gly Gly Ala Ala Ala Gly Ala Ala Lys Gly Asp Glu
            115                 120                 125

Ser Pro Ala Arg Ile Ser Asn Gly Glu Lys Thr Ala Thr Arg Pro Pro
130                 135                 140

Ala Thr Asn Gly Ser Gly Met Ala Met Ala Ser Leu Leu Asp Lys Tyr
145                 150                 155                 160

Arg Arg Glu Cys Gly Ala Ala Gly Leu Phe Ala Ile Gly Arg His His
                165                 170                 175

Asn Ser Lys Glu Asp Tyr Cys Ser Ser Thr Asn Glu Asp Thr Ser Lys
                180                 185                 190

Ser Val Glu Phe Tyr Asp Phe Leu Gln Val Asn Ala Ser Ser Ser Asp
            195                 200                 205

Thr Lys Cys Gly Ser Ser Ile Glu Glu Gln Glu Asp Asn Arg Asp Asp
210                 215                 220

Asp Gln Ala Glu Gly Gln Val Gln Leu Ile Asp Phe Met Glu Val Gly
225                 230                 235                 240

Thr Thr Ser Arg Gln
                245

<210> SEQ ID NO 36
<211> LENGTH: 264
<212> TYPE: DNA
<213> ORGANISM: Brachypodium distachyon
<220> FEATURE:
<221> NAME/KEY: misc_feature
<222> LOCATION: (1)...(264)
<223> OTHER INFORMATION: Gene Identifier: Bradi2g16120

<400> SEQUENCE: 36
atgtcttctg ggtcatctcg cagctcctcc ccaggctcaa actcggcatg gagcaagaag      60
gaggacaaga tgttcgagga tgcgcttgcc tactacggcg tgggcacccc caacctgtgg     120
gacaaggtgg ccagcgccat ggggggcagc aagtccgctg aggaggtgcg ctgccactac     180
gaggaccttt acgatgacgt gaagttgatc gagtccgggc gggtgccatt tcccaagtac     240
aggacgcagg ggttctggac ctga                                           264

<210> SEQ ID NO 37
<211> LENGTH: 87
<212> TYPE: PRT
<213> ORGANISM: Brachypodium distachyon
<220> FEATURE:
<221> NAME/KEY: DOMAIN
<222> LOCATION: (1)...(87)
<223> OTHER INFORMATION: Gene Identifier: Bradi2g16120

<400> SEQUENCE: 37

Met Ser Ser Gly Ser Ser Arg Ser Ser Pro Gly Ser Asn Ser Ala
1               5                   10                  15

Trp Ser Lys Lys Glu Asp Lys Met Phe Glu Asp Ala Leu Ala Tyr Tyr
            20                  25                  30

Gly Val Gly Thr Pro Asn Leu Trp Asp Lys Val Ala Ser Ala Met Gly
        35                  40                  45

Gly Ser Lys Ser Ala Glu Glu Val Arg Cys His Tyr Glu Asp Leu Tyr
    50                  55                  60

Asp Asp Val Lys Leu Ile Glu Ser Gly Arg Val Pro Phe Pro Lys Tyr
65                  70                  75                  80

Arg Thr Gln Gly Phe Trp Thr
                85

<210> SEQ ID NO 38
<211> LENGTH: 636
<212> TYPE: DNA
<213> ORGANISM: Brachypodium distachyon
<220> FEATURE:
<221> NAME/KEY: misc_feature
<222> LOCATION: (1)...(636)
<223> OTHER INFORMATION: Gene Identifier: Bradi4g35950

<400> SEQUENCE: 38

```
atgaggacga tctgcgatgt gtgcgagagc gcggtggcgg tgctcttctg cgcggccgac      60
gaggccgccc tctgccgctc ctgcgacgag aaggtacatc tgtgtaacaa gcttgctagt     120
cggcatgtaa gggttgggct tgcagaccct aataaattag tacgctgtga tatatgtgaa     180
aattctcctg ctttcttcta ctgtgatata gatggtacat cactttgcct gagttgtgat     240
atggctgttc atgttggtgg gaaacgaacc catggaagat atttgctgct aagacaaagg     300
gtcgaattc caggagataa accagggaat atggatgacg tacctatgca gcagatagaa     360
tctgaaaacc agagggacca aaataaggct cctcattcag taccgaagga gcaaatggtg     420
agccatcatc atgcctatga taatcatgcc tcagatggca attgcaatgg gcagggtaac     480
attgattcta aaatgtttga tcttaatatg agaccagctc gtaatcatgg gcaaggttcg     540
agttcacaga ctcaggcagt tgatcatagt gccaacaacc atgactcttc aggagtggtg     600
ccaacatgca atttggaacg agacaccaac aaataa                               636
```

<210> SEQ ID NO 39
<211> LENGTH: 211
<212> TYPE: PRT
<213> ORGANISM: Brachypodium distachyon
<220> FEATURE:
<221> NAME/KEY: DOMAIN
<222> LOCATION: (1)...(211)
<223> OTHER INFORMATION: Gene Identifier: Bradi4g35950

<400> SEQUENCE: 39

Met Arg Thr Ile Cys Asp Val Cys Glu Ser Ala Val Ala Val Leu Phe
1               5                   10                  15

Cys Ala Ala Asp Glu Ala Ala Leu Cys Arg Ser Cys Asp Glu Lys Val
            20                  25                  30

His Leu Cys Asn Lys Leu Ala Ser Arg His Val Arg Val Gly Leu Ala
        35                  40                  45

Asp Pro Asn Lys Leu Val Arg Cys Asp Ile Cys Glu Asn Ser Pro Ala
    50                  55                  60

```
Phe Phe Tyr Cys Asp Ile Asp Gly Thr Ser Leu Cys Leu Ser Cys Asp
 65                  70                  75                  80

Met Ala Val His Val Gly Gly Lys Arg Thr His Gly Arg Tyr Leu Leu
                 85                  90                  95

Leu Arg Gln Arg Val Glu Phe Pro Gly Asp Lys Pro Gly Asn Met Asp
            100                 105                 110

Asp Val Pro Met Gln Gln Ile Glu Ser Glu Asn Gln Arg Asp Gln Asn
        115                 120                 125

Lys Ala Pro His Ser Val Pro Lys Glu Gln Met Val Ser His His His
130                 135                 140

Ala Tyr Asp Asn His Ala Ser Asp Gly Asn Cys Asn Gly Gln Gly Asn
145                 150                 155                 160

Ile Asp Ser Lys Met Phe Asp Leu Asn Met Arg Pro Ala Arg Asn His
                165                 170                 175

Gly Gln Gly Ser Ser Ser Gln Thr Gln Ala Val Asp His Ser Ala Asn
            180                 185                 190

Asn His Asp Ser Ser Gly Val Val Pro Thr Cys Asn Leu Glu Arg Asp
        195                 200                 205

Thr Asn Lys
    210

<210> SEQ ID NO 40
<211> LENGTH: 264
<212> TYPE: DNA
<213> ORGANISM: Brachypodium distachyon
<220> FEATURE:
<221> NAME/KEY: misc_feature
<222> LOCATION: (1)...(264)
<223> OTHER INFORMATION: Gene Identifier: Bradi2g16120

<400> SEQUENCE: 40
atgtcttctg ggtcatctcg cagctcctcc ccaggctcaa actcggcatg gagcaagaag      60
gaggacaaga tgttcgagga tgcgcttgcc tactacggcg tgggcacccc caacctgtgg     120
gacaaggtgg ccagcgccat ggggggcagc aagtccgctg aggaggtgcg ctgccactac     180
gaggaccttt acgatgacgt gaagttgatc gagtccgggc gggtgccatt cccaagtac      240 aggacgcagg ggttctggac ctga                                            264

<210> SEQ ID NO 41
<211> LENGTH: 87
<212> TYPE: PRT
<213> ORGANISM: Brachypodium distachyon
<220> FEATURE:
<221> NAME/KEY: DOMAIN
<222> LOCATION: (1)...(87)
<223> OTHER INFORMATION: Gene Identifier: Bradi2g16120

<400> SEQUENCE: 41

Met Ser Ser Gly Ser Ser Arg Ser Ser Pro Gly Ser Asn Ser Ala
 1               5                  10                  15

Trp Ser Lys Lys Glu Asp Lys Met Phe Glu Asp Ala Leu Ala Tyr Tyr
                 20                  25                  30

Gly Val Gly Thr Pro Asn Leu Trp Asp Lys Val Ala Ser Ala Met Gly
             35                  40                  45

Gly Ser Lys Ser Ala Glu Glu Val Arg Cys His Tyr Glu Asp Leu Tyr
         50                  55                  60
```

Asp Asp Val Lys Leu Ile Glu Ser Gly Arg Val Pro Phe Pro Lys Tyr
65                  70                  75                  80

Arg Thr Gln Gly Phe Trp Thr
                85

<210> SEQ ID NO 42
<211> LENGTH: 291
<212> TYPE: DNA
<213> ORGANISM: Brachypodium distachyon
<220> FEATURE:
<221> NAME/KEY: misc_feature
<222> LOCATION: (1)...(291)
<223> OTHER INFORMATION: Gene Identifier: Bradi2g44520

<400> SEQUENCE: 42
atggcgtcca tgtcgatgaa ctcgtcgatg ccgcagtgga cggcgaagca gaacaagcag     60
ttcgagcagg cgctggcggt gtacgacaag gagacgccgg accggtggca caacatcgcg    120
cgctccgtgg ggggcaagac ggccgacgag gtcaagcgct actacgagct gctcgtccgg    180
gacgtcaagc acatcgaggc cggcaaggtg cccttcccgg cctacagatg cccccccgcc    240
ggcgccatgg ccgactacga ggccgacagg ttgaggcacc taaagatcta g             291

<210> SEQ ID NO 43
<211> LENGTH: 96
<212> TYPE: PRT
<213> ORGANISM: Brachypodium distachyon
<220> FEATURE:
<221> NAME/KEY: DOMAIN
<222> LOCATION: (1)...(96)
<223> OTHER INFORMATION: Gene Identifier: Bradi2g44520

<400> SEQUENCE: 43

Met Ala Ser Met Ser Met Asn Ser Ser Met Pro Gln Trp Thr Ala Lys
1               5                   10                  15

Gln Asn Lys Gln Phe Glu Gln Ala Leu Ala Val Tyr Asp Lys Glu Thr
                20                  25                  30

Pro Asp Arg Trp His Asn Ile Ala Arg Ser Val Gly Gly Lys Thr Ala
            35                  40                  45

Asp Glu Val Lys Arg Tyr Tyr Glu Leu Leu Val Arg Asp Val Lys His
        50                  55                  60

Ile Glu Ala Gly Lys Val Pro Phe Pro Ala Tyr Arg Cys Pro Pro Ala
65                  70                  75                  80

Gly Ala Met Ala Asp Tyr Glu Ala Asp Arg Leu Arg His Leu Lys Ile
                85                  90                  95

<210> SEQ ID NO 44
<211> LENGTH: 1338
<212> TYPE: DNA
<213> ORGANISM: Brachypodium distachyon
<220> FEATURE:
<221> NAME/KEY: misc_feature
<222> LOCATION: (1)...(1338)
<223> OTHER INFORMATION: Gene Identifier: Bradi1g13980

<400> SEQUENCE: 44
atgggagacg catccagacc cctcggcgtg gacgatgacc tcatggagct gctgtggtgc     60
aacggccatg tggtcatgca gagccagact caccggaagc tgccgccgag gcccgaaaag    120
gcggcggcgg cggcggcggt gatgcaagaa gacgaggccg ggctgtggtt ccctttctcg    180
cacgccgact cgctcgacaa ggacatcttc tcggacctct tctgcgaagc cgtgcctcag    240
gcagtgggga tcaagccgga ctgctacgga gacggcaacg gcagcaagtc gtccgacgcg    300

```
ccgagcgagc tgatgccgcc gcccaagtcg accatggcgg acggcggcga gctgtcggac      360
ctcgtgcagg cccggtccac ggggaaggcg gcggcggcgg ccatggagca ggagggcgcg      420
tcggcgtcgt cgttctgcgg gagcagcaac caggtgcagg tgcagcacgc cggccgcgtg      480
cagtccgcgg gcaccgctgc ctacggcagc agcgcccggc tgcagtcggc ggtgggcagc      540
gggattaatg caaacggcag aggccgtgag gccacggtgg cgtcgtcgtc ggggcgctcc      600
aacggctgct tcacgaacac gacgacgacg tccacggagc cgacgagcgc gagcctccgg      660
agcagcagca agcggaagcg gctcgacagc cgcaccgagg actactccga gagccccagc      720
gaggacgcgg agtcggagtc cttggcgctc atcgagcgca agcctccgct gaagctcccc      780
acggccagga ggagccgcgc agccgaggtg cacaacctct ccgagcggag agacgagac       840 aggatcaacg agaagatgaa ggccttgcaa gaactcatac ctcactgcaa caagacggac      900
aaggcgtcga tgctggacga ggccatcgag tacctgaaga cgctgcagat gcaggtgcag      960
atgatgtgga tgggcagcgg catggcgccg ccggcggtga tgttcccggg catgcaccag     1020
tacctgccgc ggcggatgcc ttccttcatg gccccgccgc ccgcggcggc ggcggcggcg     1080
cagagcctgc cggaccacta cgcgcacttc ctcggcgtca accaccacct gcagccgccg     1140
tcccaccacc atcagcatta tgcggcgcag gggatgggat actacccgtt gggggccaag     1200
gccgtgcagc aaagtccagc gcttccgatt caccacgtgc acagtactgc caatggcgcc     1260
acgcctgccc ctgctgccgc cgccgccgct accaacagta cacgccgggg aaacgggatg     1320
catccaaaca gaatatga                                                   1338
```

<210> SEQ ID NO 45
<211> LENGTH: 445
<212> TYPE: PRT
<213> ORGANISM: Brachypodium distachyon
<220> FEATURE:
<221> NAME/KEY: DOMAIN
<222> LOCATION: (1)...(445)
<223> OTHER INFORMATION: Gene Identifier: Bradi1g13980

<400> SEQUENCE: 45

```
Met Gly Asp Ala Ser Arg Pro Leu Gly Val Asp Asp Leu Met Glu
1               5                   10                  15

Leu Leu Trp Cys Asn Gly His Val Val Met Gln Ser Gln Thr His Arg
            20                  25                  30

Lys Leu Pro Pro Arg Pro Glu Lys Ala Ala Ala Ala Ala Ala Val Met
        35                  40                  45

Gln Glu Asp Glu Ala Gly Leu Trp Phe Pro Phe Ser His Ala Asp Ser
    50                  55                  60

Leu Asp Lys Asp Ile Phe Ser Asp Leu Phe Cys Glu Ala Val Pro Gln
65                  70                  75                  80

Ala Val Gly Ile Lys Pro Asp Cys Tyr Gly Asp Gly Asn Gly Ser Lys
                85                  90                  95

Ser Ser Asp Ala Pro Ser Glu Leu Met Pro Pro Lys Ser Thr Met
            100                 105                 110

Ala Asp Gly Gly Glu Leu Ser Asp Leu Val Gln Ala Arg Ser Thr Gly
        115                 120                 125

Lys Ala Ala Ala Ala Met Glu Gln Glu Gly Ala Ser Ala Ser Ser
    130                 135                 140

Phe Cys Gly Ser Ser Asn Gln Val Gln Val Gln His Ala Gly Arg Val
145                 150                 155                 160
```

Gln Ser Ala Gly Thr Ala Ala Tyr Gly Ser Ser Ala Arg Leu Gln Ser
                165                 170                 175

Ala Val Gly Ser Gly Ile Asn Ala Asn Gly Arg Gly Arg Glu Ala Thr
            180                 185                 190

Val Ala Ser Ser Ser Gly Arg Ser Asn Gly Cys Phe Thr Asn Thr Thr
        195                 200                 205

Thr Thr Ser Thr Glu Pro Thr Ser Ala Ser Leu Arg Ser Ser Ser Lys
    210                 215                 220

Arg Lys Arg Leu Asp Ser Arg Thr Glu Asp Tyr Ser Glu Ser Pro Ser
225                 230                 235                 240

Glu Asp Ala Glu Ser Glu Ser Leu Ala Leu Ile Glu Arg Lys Pro Pro
                245                 250                 255

Leu Lys Leu Pro Thr Ala Arg Arg Ser Arg Ala Ala Glu Val His Asn
            260                 265                 270

Leu Ser Glu Arg Arg Arg Arg Asp Arg Ile Asn Glu Lys Met Lys Ala
        275                 280                 285

Leu Gln Glu Leu Ile Pro His Cys Asn Lys Thr Asp Lys Ala Ser Met
    290                 295                 300

Leu Asp Glu Ala Ile Glu Tyr Leu Lys Thr Leu Gln Met Gln Val Gln
305                 310                 315                 320

Met Met Trp Met Gly Ser Gly Met Ala Pro Pro Ala Val Met Phe Pro
                325                 330                 335

Gly Met His Gln Tyr Leu Pro Arg Arg Met Pro Ser Phe Met Ala Pro
            340                 345                 350

Pro Pro Ala Ala Ala Ala Ala Gln Ser Leu Pro Asp His Tyr Ala
        355                 360                 365

His Phe Leu Gly Val Asn His His Leu Gln Pro Pro Ser His His His
    370                 375                 380

Gln His Tyr Ala Ala Gln Gly Met Gly Tyr Tyr Pro Leu Gly Ala Lys
385                 390                 395                 400

Ala Val Gln Gln Ser Pro Ala Leu Pro Ile His His Val His Ser Thr
                405                 410                 415

Ala Asn Gly Ala Thr Pro Ala Pro Ala Ala Ala Ala Ala Thr Asn
            420                 425                 430

Ser Asn Thr Pro Gly Asn Gly Met His Pro Asn Arg Ile
        435                 440                 445

<210> SEQ ID NO 46
<211> LENGTH: 1305
<212> TYPE: DNA
<213> ORGANISM: Brachypodium distachyon
<220> FEATURE:
<221> NAME/KEY: misc_feature
<222> LOCATION: (1)...(1305)
<223> OTHER INFORMATION: Gene Identifier: Bradi1g73710

<400> SEQUENCE: 46
atggggcagt gcagagcggc ggcaggagga ggagactgcc tgttcaagct gttcgggaag      60
accatccctg tgccggcgga ctcctccgga agcgtcgtcg ataaggacca acagcacagt     120
ggcagcagca cggctgaacc aaaagtacag gaaaatatcc tggggactc cacaggttca      180 cctacactgc cagaggtcgt ggacaccgac gactcgtgtg ctgtcaagaa gtcatcagcg     240
gatcaagaag aagaacagag tgacacggcc aaccagaagg agaagctgaa gaagcctgac     300
aagatcctgc cctgtcctcg gtgtaacagc atggacacca agttctgcta ctacaacaac     360
tacaacatca accagccacg ccacttctgc aagaaatgtc agaggtactg gacggctggt     420

```
ggtgccatgc gcaatgtccc cgtgggtgca ggccgccgaa agagcaagag tatatcagct    480
gcttcccact tccttcagag gatcagggcc accctgcccg gtgatcctct ctgcacccca    540
attaagacca acgccacggt tctcagcttt ggctccgaca catccacctt agatctcaca    600
gaacaaatga agcacctaaa ggacaagctc attccagtaa cccagatcaa gaacaccgat    660
gacccatcag tagggtcttg tgctgaagga tgggcaaaag gagaagagca gaaccaaatg    720
aactcaaggg aggaagttac agcagataaa tccacaaatg ttgcgcagca tccatgcatg    780
aacgggggaa ccatgtggcc attcagctgc gcaccttcac ctgcctattt cacctcaagt    840
gtagcaattc cgttctatcc agctgctgct gctgctgctt attggggcta catggttcct    900
ggagcttgga acactccatg gccaccgcag tctcaatctc aatctagctc atcacctaat    960
gctgcttctc cagtatccac aatgtccagt tgcttccaat cacgaaagca ccctagagat   1020
ggtgatgagg aaagagatac caataggaat ggcaaggtgt gggtgccaaa gacgatccgg   1080
atcgatgacg cagacgaggt ggccaggagt tccatctggt cactgattgg gatcaacggc   1140
gacaaggttg ggacagatga tggcagaggg tgtaagatca cgagggtttt ttatccaaag   1200
gatgaggcaa agacgacaac tcacagagtt aacaatagcc tcccgttctt gaagggggaac   1260
ccagctgcac tgtcacgctc agtgaccttc aagagagat cttga                    1305
```

<210> SEQ ID NO 47
<211> LENGTH: 434
<212> TYPE: PRT
<213> ORGANISM: Brachypodium distachyon
<220> FEATURE:
<221> NAME/KEY: DOMAIN
<222> LOCATION: (1)...(434)
<223> OTHER INFORMATION: Gene Identifier: Bradi1g73710

<400> SEQUENCE: 47

Met Gly Gln Cys Arg Ala Ala Gly Gly Gly Asp Cys Leu Phe Lys
1               5                   10                  15

Leu Phe Gly Lys Thr Ile Pro Val Pro Ala Asp Ser Ser Gly Ser Val
            20                  25                  30

Val Asp Lys Asp Gln Gln His Ser Gly Ser Ser Thr Ala Glu Pro Lys
        35                  40                  45

Val Gln Glu Asn Ile Pro Gly Asp Ser Thr Gly Ser Pro Thr Leu Pro
    50                  55                  60

Glu Val Val Asp Thr Asp Asp Ser Cys Ala Val Lys Lys Ser Ser Ala
65                  70                  75                  80

Asp Gln Glu Glu Glu Gln Ser Asp Thr Ala Asn Gln Lys Glu Lys Leu
                85                  90                  95

Lys Lys Pro Asp Lys Ile Leu Pro Cys Pro Arg Cys Asn Ser Met Asp
            100                 105                 110

Thr Lys Phe Cys Tyr Tyr Asn Asn Tyr Asn Ile Asn Gln Pro Arg His
        115                 120                 125

Phe Cys Lys Lys Cys Gln Arg Tyr Trp Thr Ala Gly Gly Ala Met Arg
    130                 135                 140

Asn Val Pro Val Gly Ala Gly Arg Arg Lys Ser Lys Ser Ile Ser Ala
145                 150                 155                 160

Ala Ser His Phe Leu Gln Arg Ile Arg Ala Thr Leu Pro Gly Asp Pro
                165                 170                 175

Leu Cys Thr Pro Ile Lys Thr Asn Ala Thr Val Leu Ser Phe Gly Ser
            180                 185                 190

```
Asp Thr Ser Thr Leu Asp Leu Thr Glu Gln Met Lys His Leu Lys Asp
            195                 200                 205

Lys Leu Ile Pro Val Thr Gln Ile Lys Asn Thr Asp Asp Pro Ser Val
        210                 215                 220

Gly Ser Cys Ala Glu Gly Trp Ala Lys Gly Glu Gln Asn Gln Met
225                 230                 235                 240

Asn Ser Arg Glu Glu Val Thr Ala Asp Lys Ser Thr Asn Val Ala Gln
                245                 250                 255

His Pro Cys Met Asn Gly Gly Thr Met Trp Pro Phe Ser Cys Ala Pro
            260                 265                 270

Ser Pro Ala Tyr Phe Thr Ser Ser Val Ala Ile Pro Phe Tyr Pro Ala
        275                 280                 285

Ala Ala Ala Ala Ala Tyr Trp Gly Tyr Met Val Pro Gly Ala Trp Asn
290                 295                 300

Thr Pro Trp Pro Pro Gln Ser Gln Ser Gln Ser Ser Ser Ser Pro Asn
305                 310                 315                 320

Ala Ala Ser Pro Val Ser Thr Met Ser Ser Cys Phe Gln Ser Arg Lys
                325                 330                 335

His Pro Arg Asp Gly Asp Glu Glu Arg Asp Thr Asn Arg Asn Gly Lys
            340                 345                 350

Val Trp Val Pro Lys Thr Ile Arg Ile Asp Asp Ala Asp Glu Val Ala
        355                 360                 365

Arg Ser Ser Ile Trp Ser Leu Ile Gly Ile Asn Gly Asp Lys Val Gly
370                 375                 380

Thr Asp Asp Gly Arg Gly Cys Lys Ile Thr Arg Val Phe Tyr Pro Lys
385                 390                 395                 400

Asp Glu Ala Lys Thr Thr Thr His Arg Val Asn Asn Ser Leu Pro Phe
                405                 410                 415

Leu Lys Gly Asn Pro Ala Ala Leu Ser Arg Ser Val Thr Phe Gln Glu
            420                 425                 430

Arg Ser
```

<210> SEQ ID NO 48
<211> LENGTH: 1071
<212> TYPE: DNA
<213> ORGANISM: Brachypodium distachyon
<220> FEATURE:
<221> NAME/KEY: misc_feature
<222> LOCATION: (1)...(1071)
<223> OTHER INFORMATION: Gene Identifier: Bradi1g26570

<400> SEQUENCE: 48

```
atggccgccg gtgcgggggg tgcggcagcg gccgcggcgg cggtgcaaca cgccggaccg      60
gcggggaggg ttggcggagg cggatcttcg tcggcgggag gaggagcggc ggcgccggac     120
ccgcgggcgg aggcgctgcg gtgcccgcgg tgcgactcgg caaacaccaa gttctgctac     180
tacaacaact actccctctc gcagccgcgg cacttctgca aggcgtgcaa gcgctactgg     240
acacgcgggg gcacccteeg caacgtcccc gtcggcggcg gctgccgcaa gaacaaacgc     300
tccaggagtt ccagcggggg cggcggcagg gtcgtctcgt caagtctgcc cgccgctgcc     360
gctgctggtg gcggcacggc ttcgtcctcg ctgccgctac cgccgcacgg gtcggcgtct     420
tcggcgctgc aggggctcca ccacgggagc agctcgctcg cgtcgctgct gctcgggacc     480
ggcgggggag gcgaccacct cgggctgttc catcaggcca tgcagtccgt ggtctccgac     540
aacgccgccg cctacgagat gcacaaccag cagcagcagc atcaggcgca ggtggatcag     600
```

-continued

```
ctgctggggc tcggctacgg gtcgcactcg cagatccaaa tgaataagcc gtggctcggc    660
catgacggcg cggggggget cttcgacgge ttctacgcgc cgctgctgtc gggctgctcc    720
atcgtgccgg ggctggagga gctgcacgtc aaggcggagg ccaccgccgg ggaaaatcac    780
catcagcaca agaaggacgg ggagcagcag cagcagcaga gcggcggcag ctgggagcag    840
cacccgaatt cctcctcctc caacgtggag gcctgcaaca caacatcat ggcgtctgaa     900 gcgctcatgg ccgccatgaa cccggcggcg cggtcagca gcaacgcggc cacggcgccg     960
actactgtgt cctcctccca gctcatgtac tgggcaacg gcggcggcgc cccgcggcg     1020 tggccggaca tcggcgccaa ctgcggatcg tccatcgcca ccttcttcta g            1071
```

<210> SEQ ID NO 49
<211> LENGTH: 356
<212> TYPE: PRT
<213> ORGANISM: Brachypodium distachyon
<220> FEATURE:
<221> NAME/KEY: DOMAIN
<222> LOCATION: (1)...(356)
<223> OTHER INFORMATION: Gene Identifier: Bradi1g26570

<400> SEQUENCE: 49

```
Met Ala Ala Gly Ala Gly Gly Ala Ala Ala Ala Ala Ala Val Gln
1               5                   10                  15

His Ala Gly Pro Ala Gly Arg Val Gly Gly Gly Ser Ser Ser Ala
                20                  25                  30

Gly Gly Gly Ala Ala Ala Pro Asp Pro Arg Ala Glu Ala Leu Arg Cys
        35                  40                  45

Pro Arg Cys Asp Ser Ala Asn Thr Lys Phe Cys Tyr Tyr Asn Asn Tyr
50                  55                  60

Ser Leu Ser Gln Pro Arg His Phe Cys Lys Ala Cys Lys Arg Tyr Trp
65                  70                  75                  80

Thr Arg Gly Gly Thr Leu Arg Asn Val Pro Val Gly Gly Gly Cys Arg
                85                  90                  95

Lys Asn Lys Arg Ser Arg Ser Ser Gly Gly Gly Arg Val Val
                100                 105                 110

Ser Ser Ser Ser Ala Ala Ala Ala Ala Gly Gly Thr Ala Ser
            115                 120                 125

Ser Ser Leu Pro Leu Pro Pro His Gly Ser Ala Ser Ser Ala Leu Gln
        130                 135                 140

Gly Leu His His Gly Ser Ser Ser Leu Ala Ser Leu Leu Leu Gly Thr
145                 150                 155                 160

Gly Gly Gly Gly Asp His Leu Gly Leu Phe His Gln Ala Met Gln Ser
                165                 170                 175

Val Val Ser Asp Asn Ala Ala Ala Tyr Glu Met His Asn Gln Gln Gln
                180                 185                 190

Gln His Gln Ala Gln Val Asp Gln Leu Leu Gly Leu Gly Tyr Gly Ser
        195                 200                 205

His Ser Gln Ile Gln Met Asn Lys Pro Trp Leu Gly His Asp Gly Ala
210                 215                 220

Gly Gly Leu Phe Asp Gly Phe Tyr Ala Pro Leu Leu Ser Gly Cys Ser
225                 230                 235                 240

Ile Val Pro Gly Leu Glu Glu Leu His Val Lys Ala Glu Ala Thr Ala
                245                 250                 255

Gly Glu Asn His His Gln His Lys Lys Asp Gly Glu Gln Gln Gln Gln
                260                 265                 270
```

```
Gln Ser Gly Gly Ser Trp Glu Gln His Pro Asn Ser Ser Ser Asn
            275                 280                 285

Val Glu Ala Cys Asn Asn Ile Met Ala Ser Glu Ala Leu Met Ala
    290                 295                 300

Ala Met Asn Pro Ala Ala Val Ser Ser Asn Ala Ala Thr Ala Pro
305                 310                 315                 320

Thr Thr Val Ser Ser Gln Leu Met Tyr Trp Gly Asn Gly Gly
                325                 330                 335

Ala Pro Ala Ala Trp Pro Asp Ile Gly Ala Asn Cys Gly Ser Ser Ile
            340                 345                 350

Ala Thr Phe Phe
        355

<210> SEQ ID NO 50
<211> LENGTH: 714
<212> TYPE: DNA
<213> ORGANISM: Brachypodium distachyon
<220> FEATURE:
<221> NAME/KEY: misc_feature
<222> LOCATION: (1)...(714)
<223> OTHER INFORMATION: Gene Identifier: Bradi1g10470

<400> SEQUENCE: 50
atgtgcacaa gggtcactg gaggccgtca gaggacgaga agctcaagga gctcgtcgtg      60
cgatacgggc cgcacaactg gaacgccatc gccgagaagc tccagggccg atcaggggaag   120 agctgcaggc tgaggtggtt caaccagctg acccccggga tcaaccggag cccttctcg     180 gaggaagagg aggagctgct cctggcctcg caccgcgtcc acggcaaccg gtgggccgtc    240
atcgccaggc tcttcccggg ccgcaccgac aacgccgtca gaaccactg gcatgtgatc     300 atggcgcgcc gctgcaggga gcggatgagg atatcctcca gcaagcgggc aggtcccggt    360
aaagacgaga tcagcccaag gaaccacgac gccgctgccg gcgagaagcc gagacccgca    420
gccgacgcga gtcgcatggc cgccttgctt gacaagtaca aagggaatt tgctgggccc     480 tttgcgatca gccatcacag cagcaaggag ggttactgct cgtctacgaa tgaagatacg    540
aatagatcgg tggagttcta cgatttcctc caggtgaacg tgagctcgag cgacaccaag    600
tgcagctcga gcatcgagga gcaggaagac aacggccgag acgacgacga tcaacaagcg    660
gaagggcaag tggcgctcat agatttcatg gaggttggga cttctcatca gtga          714

<210> SEQ ID NO 51
<211> LENGTH: 237
<212> TYPE: PRT
<213> ORGANISM: Brachypodium distachyon
<220> FEATURE:
<221> NAME/KEY: DOMAIN
<222> LOCATION: (10)...(237)
<223> OTHER INFORMATION: Gene Identifier: Bradi1g10470

<400> SEQUENCE: 51

Met Cys Thr Arg Gly His Trp Arg Pro Ser Glu Asp Glu Lys Leu Lys
1               5                   10                  15

Glu Leu Val Val Arg Tyr Gly Pro His Asn Trp Asn Ala Ile Ala Glu
            20                  25                  30

Lys Leu Gln Gly Arg Ser Gly Lys Ser Cys Arg Leu Arg Trp Phe Asn
        35                  40                  45

Gln Leu Asp Pro Arg Ile Asn Arg Ser Pro Phe Ser Glu Glu Glu Glu
    50                  55                  60
```

```
Glu Leu Leu Leu Ala Ser His Arg Val His Gly Asn Arg Trp Ala Val
 65                 70                  75                  80

Ile Ala Arg Leu Phe Pro Gly Arg Thr Asp Asn Ala Val Lys Asn His
             85                  90                  95

Trp His Val Ile Met Ala Arg Arg Cys Arg Glu Arg Met Arg Ile Ser
            100                 105                 110

Ser Ser Lys Arg Ala Gly Pro Gly Lys Asp Glu Ile Ser Pro Arg Asn
        115                 120                 125

His Asp Ala Ala Ala Gly Glu Lys Pro Arg Pro Ala Ala Asp Ala Ser
    130                 135                 140

Arg Met Ala Ala Leu Leu Asp Lys Tyr Arg Arg Glu Phe Ala Gly Pro
145                 150                 155                 160

Phe Ala Ile Ser His His Ser Ser Lys Glu Gly Tyr Cys Ser Ser Thr
                165                 170                 175

Asn Glu Asp Thr Asn Arg Ser Val Glu Phe Tyr Asp Phe Leu Gln Val
            180                 185                 190

Asn Val Ser Ser Ser Asp Thr Lys Cys Ser Ser Ile Glu Glu Gln
        195                 200                 205

Glu Asp Asn Gly Arg Asp Asp Asp Gln Gln Ala Glu Gly Gln Val
    210                 215                 220

Ala Leu Ile Asp Phe Met Glu Val Gly Thr Ser His Gln
225                 230                 235

<210> SEQ ID NO 52
<211> LENGTH: 1992
<212> TYPE: DNA
<213> ORGANISM: Zea mays
<220> FEATURE:
<221> NAME/KEY: misc_feature
<222> LOCATION: (1)...(1992)
<223> OTHER INFORMATION: Gene Identifier: Ubiquitin promoter and 5'UTR

<400> SEQUENCE: 52
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctatact actacaataa     180
tatcagtgtt ttagagaatc atataaatga acagttagac atggtctaaa ggacaattga     240 gtatttgac aacaggactc tacagtttta tcttttagt gtgcatgtgt tctccttttt      300
ttttgcaaat agcttcacct atataatact tcatccattt tattagtaca tccatttagg     360
gtttagggtt aatggttttt atagactaat ttttttagta catctatttt attctatttt     420
agcctctaaa ttaagaaaac taaaactcta ttttagtttt tttatttaat aatttagata     480
taaaatagaa taaaataaag tgactaaaaa ttaaacaaat acccctttaag aaattaaaaa     540 aactaaggaa acatttttct tgtttcgagt agataatgcc agcctgttaa acgccgtcga     600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacggca cggcagctac gggggattcc tttcccaccg     840
ctccttcgct ttcccttcct cgcccgccgt aataaataga caccccctcc acccctcttt     900
tccccaacct cgtgttgttc ggagcgcaca cacacacaac cagatctccc ccaaatccac     960
ccgtcggcac ctccgcttca aggtacgccg ctcgtcctcc cccccccccc ctctctacct    1020
```

-continued

```
tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
atggctctag ccgttccgca gacgggatcg atttcatgat ttttttttgtt tcgttgcata    1260 gggtttggtt tgcccttttc ctttatttca atatatgccg tgcacttgtt tgtcgggtca    1320
tcttttcatg cttttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggttta ctgatgcata tacagagatg cttttttgttc    1560 gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttttag ccctgccttc    1920 atacgctatt tatttgcttg gtactgtttc ttttgtcgat gctcaccctg ttgtttggtg    1980
ttacttctgc ag                                                        1992
```

COMPOSITIONS AND METHODS FOR INCREASING PLANT GROWTH AND YIELD

CROSS-REFERENCE TO RELATED APPLICATIONS

This application is a national stage filing under 35 U.S.C. 371 of PCT/US2015/039571 filed Jul. 8, 2015, which International Application was published by the International Bureau in English on Jan. 14, 2016, and application claims priority from U.S. Provisional Application No. 62/022,925, filed Jul. 10, 2014, which applications are hereby incorporated in their entirety by reference in this application.

FIELD OF THE INVENTION

The invention is drawn to compositions and methods for controlling gene expression involved in plant growth and development.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield as well as tolerance to abiotic stress. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigor may also be important factors in determining yield. Optimizing the abovementioned factors may therefore contribute to increasing crop yield. Abiotic stresses encountered by plants may include high or low temperature stress, drought or overwatering, and salt stress. Plant responses to these and other abiotic stresses can have important effects on yield, as these stresses can cause significant yield losses. It is therefore desirable to produce plants and plant varieties that maintain their growth when faced with abiotic stresses in order to maximize their yield under non-optimal growing conditions.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in plant growth and development. Therefore, methods are needed for modulating such genes.

SUMMARY OF THE INVENTION

Compositions and methods for increasing plant growth for higher crop yield are provided. Compositions comprise transcription factors, constructs comprising the transcription factors, and transgenic plants, seeds, and plant parts containing the transcription factors. The transcription factors can be used to alter plant growth and/or stress tolerance by modulating the expression level and/or expression pattern of one or more transcription factor in a plant of interest. Transcription factors that regulate genes involved in plant growth, photosynthesis, or other genes can be modulated to increase plant growth, increase plant mass, improve plant stress tolerance, and increase plant yield.

Embodiments of the invention include:

1. A method of improving plant growth in a plant of interest by altering or modulating the expression of at least one nucleotide sequence encoding a polypeptide selected from the group of SEQ ID NOs: 2, 4, 6, 8, 10, 12, 14, 16, 21, 23, 27, 29, 31, 33, 35, 37, 39, 43, 45, 47, 49, or 51, or a fragment or variant thereof.
2. The method of embodiment 1 wherein said nucleotide sequence encodes a polypeptide selected from the group of SEQ ID NOs: 2, 4, 6, 8, 10, 12, 14, or 16, or a fragment or variant thereof.
3. The method of embodiment 1 wherein the at least one nucleotide sequence is upregulated such that expression of the TF is increased relative to a control plant cell.
4. The method of embodiment 1 wherein the at least one nucleotide sequence is downregulated such that expression of the TF is decreased relative to a control plant cell.
5. The method of embodiment 1, 2, 3, or 4 wherein said modulating is achieved by the stable insertion of at least one expression construct comprising a promoter that drives expression in a plant cell, operably linked to at least one nucleotide sequence encoding at least one transcription factor wherein said transcription factor comprises a polypeptide selected from the group of SEQ ID NOs: 2, 4, 6, 8, 10, 12, 14, 16, 21, 23, 27, 29, 31, 33, 35, 37, 39, 43, 45, 47, 49, or 51.
6. The method of any one of embodiments 1 or 2, wherein said fragment or variant has at least 80% sequence identity to the nucleotide sequence or the polypeptide sequence.
7. The method of any one of embodiments 1 or 2, wherein said fragment or variant has at least 90% sequence identity to the nucleotide sequence or the polypeptide sequence.

8. The method of any one of embodiments 1 or 2, wherein said fragment or variant has at least 95% sequence identity to the nucleotide sequence or the polypeptide sequence.
9. The method of any one of embodiments 1-4, wherein said modulating is achieved by the stable insertion of a DNA construct comprising at least one promoter that drives expression in a plant cell, operably linked to one or more amiRNA cassettes designed against at least one nucleotide encoding a transcription factor polypeptide selected from the group of SEQ ID NOs: 2, 4, 6, 8, 10, 12, 14, 16, 21, 23, 27, 29, 31, 33, 35, 37, 39, 43, 45, 47, 49, or 51.
10. The method of any one of embodiments 1-4 wherein said modulating is achieved by the stable insertion of a transformation construct comprising one or more promoters that are operable in a plant cell, operably linked to one or more RNAi cassettes designed against at least one transcription factor of interest.
11. The method of any one of embodiments 1-4 wherein said modulating is achieved by transforming a plant species of interest with a self-replicating transformation construct derived from a plant virus and comprising at least one promoter that is operable in a plant cell, operably linked to at least one open reading frame encoding at least one transcription factor of interest.
12. The method of any one of embodiments 1-4 wherein said modulating is achieved by transforming a plant species of interest with a self-replicating transformation construct derived from a plant virus and comprising at least one promoter that is operable in a plant cell, operably linked to at least one amiRNA cassette designed against at least one transcription factor of interest.
13. The method of any one of embodiments 1-4 wherein said modulating is achieved by transforming a plant species of interest with a self-replicating transformation construct derived from a plant virus and comprising at least one promoter that is operable in a plant cell, operably linked to at least one RNAi cassette designed against at least one transcription factor of interest.
14. The method of any one of embodiments 1-4 wherein said modulating is achieved by inserting at least one cis-regulatory element into the genome of a plant cell, at a location such that the cis-regulatory element can alter the expression level and/or expression profile of at least one transcription factor of interest.
15. The method of any one of embodiments 9-13 wherein the at least one promoter is a constitutive promoter.
16. The method of any one of embodiments 9-13 wherein the at least one promoter or is a non-constitutive promoter.
17. The method of embodiment 16 wherein the at least one promoter is a developmentally-regulated promoter.
18. The method of embodiment 16 wherein the at least one promoter is a circadian-regulated or diurnally-regulated promoter.
19. The method of embodiment 16 wherein the at least one promoter is a tissue-specific promoter.
20. The method of embodiment 16 wherein the at least one promoter is an inducible promoter.
21. The method of embodiment 16 wherein the at least one promoter is a light-regulated promoter.
22. The method of embodiment 16 wherein the at least one promoter comprises the sequence set forth in SEQ ID NO: 17.
23. The method of embodiment 16 wherein the at least one promoter comprises the sequence set forth in SEQ ID NO: 18.
24. The method of embodiment 16 wherein the at least one promoter comprises the sequence set forth in SEQ ID NO: 19.
25. The method of any one of embodiments 1-24, wherein the plant of interest is a monocotyledonous plant.
26. The method of any one of embodiments 1-24, wherein the plant of interest is a dicotyledonous plant.
27. An isolated polynucleotide, said polynucleotide comprising a nucleotide sequence encoding a transcription factor, having at least 90% sequence identity to an amino acid sequence set forth in SEQ ID NOs: 2, 4, 6, 8, 10, 12, 14, 16, 21, 23, 27, 29, 31, 33, 35, 37, 39, 43, 45, 47, 49, or 51.
28. The isolated polynucleotide of embodiment 27, wherein said polypeptide has at least 95% identity to an amino acid sequence set forth in SEQ ID NOs: 2, 4, 6, 8, 10, 12, 14, 16, 21, 23, 27, 29, 31, 33, 35, 37, 39, 43, 45, 47, 49, or 51.
29. The method of embodiment 1 wherein said improving plant growth comprises providing tolerance of high-pH conditions to said plant of interest.
30. The method of embodiment 29 wherein the plant can tolerate a pH greater than 8.
31. The method of embodiment 29 wherein the plant can tolerate a pH greater than 8.5.
32. The method of embodiment 29 wherein the plant can tolerate a pH greater than 9.
33. The method of embodiment 29 wherein the plant can tolerate a pH greater than 9.5.
34. The method of embodiment 1 wherein said improving plant growth comprises providing tolerance of high-salt conditions to said plant of interest.
35. The method of embodiment 34 wherein said high-salt conditions comprise $Na^+$ concentrations greater than 50 ppm.
36. The method of embodiment 34 wherein said high-salt conditions comprise $Na^+$ concentrations greater than 55 ppm.
37. The method of embodiment 34 wherein said high-salt conditions comprise $Na^+$ concentrations greater than 60 ppm.
38. The method of embodiment 34 wherein said high-salt conditions comprise $SO_4^{2-}$ concentrations greater than 90 ppm.
39. The method of embodiment 34 wherein said high-salt conditions comprise $SO_4^{2-}$ concentrations greater than 100 ppm.
40. The method of embodiment 34 wherein said high-salt conditions comprise $SO_4^{2-}$ concentrations greater than 110 ppm.
41. The method of embodiment 34 wherein said high-salt conditions comprise $SO_4^{2-}$ concentrations greater than 120 ppm.
42. The method of embodiment 34 wherein said high-salt conditions comprise $SO_4^{2-}$ concentrations greater than 130 ppm.
43. The method of embodiment 34 wherein said high-salt conditions comprise $SO_4^{2-}$ concentrations greater than 140 ppm.
44. The method of embodiment 34 wherein said high-salt conditions comprise $SO_4^{2-}$ concentrations greater than 150 ppm.

45. The method of embodiment 34 wherein said high-salt conditions comprise $Cl^-$ concentrations greater than 20 ppm.
46. The method of embodiment 34 wherein said high-salt conditions comprise $Na^+$ concentrations greater than 50 ppm, $SO_4^{2-}$ concentrations greater than 90 ppm, and $Cl^-$ concentrations greater than 20 ppm.

DETAILED DESCRIPTION OF THE INVENTION

Increasing crop plant growth for higher yield is a primary goal of plant breeding and of plant biotechnology. As an extremely complex trait, yield potential is controlled by both positive and negative feedback, and is regulated by many different genes across multiple metabolic pathways. The successful manipulation of this trait may therefore require the concurrent manipulation of the expression of many different genes. A promising method to manipulate the expression of many genes simultaneously is to alter the expression of a transcription factor (TF) or of multiple TFs that regulate the expression of multiple genes associated with the trait of interest (i.e., elevated crop growth and yield). The present invention describes methods to alter TF expression in plants that lead to improved plant growth and yield. Recombinant nucleotide sequences encoding the TFs are provided. Methods to alter the expression level and/or profile of said TFs in order to improve plant growth are described. Additionally, plants, seeds, and plant parts that have been modified to modulate the expression of at least one TF of the invention are provided.

By "yield" or "crop yield" is intended the measurement of the amount of a crop that was harvested per unit of land area. Crop yield is the measurement often used for grains or cereals and is typically measured as the amount of plant harvested per unit area for a given time, i.e., metric tons per hectare or kilograms per hectare. Crop yield can also refer to the actual seed or biomass produced or generated by the plant.

By "tolerant" or "tolerance" is intended an ability of a plant to grow under a particular set of environmental conditions that are not typically seen as favorable for plant growth and under which a control plant is not capable of growing normally. A tolerant plant may exhibit improved yield relative to a control plant when grown under such environmental conditions.

A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

A "recombinant polynucleotide construct" comprises two or more operably linked nucleic acid segments which are not found operably linked in nature. Non-limiting examples of recombinant polynucleotide constructs include a polynucleotide of interest or active variant or fragment thereof operably linked to heterologous sequences which aid in the expression, autologous replication, and/or genomic insertion of the sequence of interest. Such heterologous and operably linked sequences include, for example, promoters, termination sequences, enhancers, etc, or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 1, 2, 3, 4, 5, 6, 7, 8, 9, 10, 15, 20 or amino acids.

The invention comprises synthetic oligonucleotides or nucleotide sequences. A synthetic sequence is one that is produced or reproduced in a laboratory setting. While the nucleotide sequence may have an altered nucleotide sequence relative to the parent sequence, the synthetic sequence may be identical to the naturally occurring sequence. In both instances, however, the structure of the synthetic sequence is altered or different from that found in the sequence that is directly isolated from its natural setting.

By "altering" or "modulating" the expression level of a TF is intended that the expression is upregulated or downregulated relative to the expression level of said TF in a wild-type or control plant. It is recognized that in some instances, plant growth and yield are increased by increasing the expression levels of one or more of the TFs of the invention, i.e. upregulating expression. Likewise, in some instances, plant growth and yield may be increased by decreasing the expression levels of one or more of the TFs of the invention, i.e. downregulating expression. Thus, the invention encompasses the upregulation or downregulation of one or more of the TFs of the invention. Further, the methods include the upregulation of at least one TF and the downregulation of at least one TF in a plant of interest. By modulating the concentration and/or activity of at least one of the TFs of the invention in a transgenic plant is intended that the concentration and/or activity is increased or decreased by at least 1%, 5%, 10%, 20%, 30%, 40%, 50%, 60%, 70%, 80%, or 90% relative to a native control plant, plant part, or cell which did not have the sequence of the invention introduced. It is recognized that the expression levels of the TFs can be controlled by the choice of promoter or the use of enhancers of the invention. For example, if a 30% increase is desired, a promoter will be selected to provide the appropriate expression level. The expression level of the TF may be measured directly, for example, by assaying for the level of the TF in the plant.

The compositions of the invention are used to alter expression of genes of interest in a plant, particularly genes involved in photosynthesis. Therefore, the expression of a TF may be modulated as compared to a control plant. A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, seed, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The invention encompasses isolated or substantially purified transcription factor or enhancer polynucleotide or amino acid compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived.

Fragments and variants of the disclosed polynucleotides and amino acid sequences encoded thereby are also encompassed by the present invention. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native TF or enhancer. Biologically active variants of a native TF or enhancer sequence of the invention will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. A biologically active variant of a protein of the invention may differ from that protein by as few as 1-15 amino acid residues, as few as 1-10, such as 6-10, as few as 5, as few as 4, 3, 2, or even 1 amino acid residue.

As indicated, the TF factors of the invention are modulated, i.e., upregulated or downregulated, in a plant of interest. It may be desirable to upregulate at least one TF while simultaneously downregulating at least one different TF. Methods for increasing the expression or upregulating a TF are known in the art and any can be used in the methods of the invention. In one embodiment, upregulation can be achieved by either stably or transiently transforming a plant or plant cell with an expression cassette comprising a promoter that drives expression in the plant operably linked to at least one TF of the invention. Alteration of the expression of one or more of the TFs of the present invention may be achieved through the use of precise genome-editing technologies to modulate the expression of the endogenous TF sequence. In this manner, a nucleic acid sequence will be inserted proximal to a native plant sequence encoding the TF of interest through the use of methods available in the art. Such methods include, but are not limited to, meganucleases designed against the plant genomic sequence of interest (D'Halluin et al (2013) *Plant Biotechnol J* 11: 933-941); CRISPR-Cas9, TALENs, and other technologies for precise editing of genomes (Feng, et al. (2013) *Cell Research* 23:1229-1232, Podevin, et al. (2013) *Trends Biotechnology* 31: 375-383, Wei et al. (2013) *J Gen Genomics* 40: 281-289, Zhang et al (2013) WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. *Plant J* (2011) 701: 147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta, H. (2002) *Plant Mol Biol* 48:173-182). The insertion of said nucleic acid sequences will be used to achieve the desired result of overexpression of one or more of the TFs of the present invention.

Enhancers include any molecule capable of enhancing gene expression when inserted into the genome of a plant. Thus, an enhancer can be inserted in a region of the genome upstream or downstream of at least one TF sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous TF or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy, M. and Hannah, L. C. (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi, S. (2011)*Methods Mol. Biol.* 701:285-300). In some embodiments, the present invention comprises a subdomain, fragment, or duplicated enhancer element (Benfrey et al. (1990) *EMBO J* 9:1677-1684).

The invention further provides methods for modulating TF expression in a plant by inserting a promoter or enhancer into a plant genome such that it modulates expression of an endogenous or exogenous sequence. As indicated above, methods for determining an insertion site for a promoter or enhancer using the sequences provided herein and methods for inserting a promoter or enhancer sequence into a plant genome at a given insertion site are known in the art.

Downregulation or reduction of the activity of a TF (also known as gene silencing or gene suppression) is also encompassed by the methods of the invention. Many techniques for gene silencing are well known to one of skill in the art, including, but not limited to, antisense technology (see, e.g., Sheehy et al. (1988) Proc. Natl. Acad. Sci. USA 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507), virus-induced gene silencing (Burton et al. (2000) *Plant Cell* 12:691-705; and Baulcombe (1999) *Curr. Opin. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, U.S. Patent Publication No. 20030175965; Panstruga et al. (2003) *Mol. Biol. Rep.* 30:135-140; Wesley et al. (2001) *Plant J.* 27:581-590; Wang and Waterhouse (2001) *Curr. Opin. Plant Biol.* 5:146-150; U.S. Patent Publication No. 20030180945; and, WO 02/00904, all of which are herein incorporated by reference); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179: 53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference; and other methods or combinations of the above methods known to those of skill in the art.

Modulation of the expression of one or more of the TFs of the present invention may also be achieved through the use of self-replicating DNA sequences derived from plant viruses rather than through the stable insertion of the gene or genes of interest into the plant nuclear genome. Sequences derived from plant viruses such as the Geminivirus have been used successfully to achieve expression of multiple genes of interest in a plant (Mozes-Koch et al (2012) *Plant Physiol* 158:1883-1892). By inserting a gene or genes encoding one or more of the TFs of the present invention into a self-replicating construct derived from a plant virus, upregulation of said TFs may be achieved in the plant species of interest by transforming the virus-derived construct into the plant cells and selecting for transformed cells.

It is recognized that with the polynucleotides of the invention, antisense constructs, complementary to at least a portion of the messenger RNA (mRNA) for the TF sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% or greater sequence identity to the corresponding sequences to be silenced may be used. Furthermore, portions of the antisense nucleotides may be used to disrupt the expression of the target gene encoding a TF.

The polynucleotides of the present invention may also be used in the sense orientation to suppress the expression of endogenous genes in plants. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Such methods may be used to reduce the expression of at least one TF.

The polynucleotides of the invention can be used to isolate corresponding sequences from other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that transcription activation or enhancer activities and which hybridize under stringent conditions to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding TF or enhancer sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences.

The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

The polynucleotides of the invention can be provided in expression cassettes for expression in a plant of interest. The cassette will include 5' and 3' regulatory sequences operably linked to a TF polynucleotide of the invention. "Operably linked" is intended to mean a functional linkage between two or more elements. The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the TF polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a TF polynucleotide of the invention, and a transcriptional and translational termination region (i.e., termination region) functional in plants.

A number of promoters may be used in the practice of the invention. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18;

Orozco et al. (1993) *Plant Mol. Biol.* 23(6):1129-1138; and Matsuoka et al. (1993) *Proc. Natl. Acad. Sci. USA* 90(20): 9586-9590.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be highly important for the function of the gene or gene product in planta. One strategy that may be used to provide a desired expression profile is the use of synthetic promoters containing cis-regulatory elements that drive the desired expression levels at the desired time and place in the plant. A number of researchers have identified cis-regulatory elements that can be used to alter gene expression in planta (Vandepoele et al (2009) *Plant Physiol* 150:535-546; Rushton et al (2002) *Plant Cell* 14:749-762). The use of cis-regulatory elements to alter promoter expression profiles has also been reviewed (Venter (2007) *Trends Plant Sci* 12:118-124). The rapid development of new technologies for transcriptomic studies and of new methods to analyze such datasets has enabled the discovery of new cis-regulatory elements. It is well understood that microarray datasets used previously did not have the same resolution as transcriptomic data generated using RNA-Seq. The use of these newer technologies to generate transcriptomic data and the development of new software algorithms for the analysis of transcriptomic data has enabled the discovery of novel cis-regulatory elements including those described herein.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the TF can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27 37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof. "Transient transformation" is intended to mean that the nucleotide construct introduced into a plant is not stably integrated into the genome of the plant, but is maintained in the plant cell for a sufficient period of time to allow for the expression of the introduced genes.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* sp.), eucalyptus (*Eucalyptus* sp.), oats, barley, vegetables, ornamentals, and conifers.

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1

GRMZM2G143718 Expression in *Brachypodium distachyon*

The GRMZM2G143718 coding sequence was codon-optimized for expression in *Brachypodium distachyon* (SEQ ID NO: 1). The resulting coding sequence was cloned into four separate binary vectors, each with a different promoter and 5'UTR. These binary vectors are described in Table 1.

TABLE 1

GRMZM2G143718 Constructs

| Construct Number | Promoter and 5'UTR | Coding Sequence |
|---|---|---|
| 130020 | ZmUbi (SEQ ID NO: 52) | GRMZM2G143718 (SEQ ID NO: 1) |
| 130028 | 4xRGCGR (SEQ ID NO: 19) | GRMZM2G143718 (SEQ ID NO: 1) |
| 130036 | ZmCA1 (SEQ ID NO: 18) | GRMZM2G143718 (SEQ ID NO: 1) |
| 130044 | ZmPepC (SEQ ID NO: 17) | GRMZM2G143718 (SEQ ID NO: 1) |

The vectors described in Table 1 were used to transform *B. distachyon* cells. Transformed *B. distachyon* cells were regenerated using plant tissue culture techniques to produce transgenic *B. distachyon* plants containing the GRMZM2G143718 transgene cassette in these vectors. Introduction of the transgene cassette was confirmed by PCR using DNA extracted from the regenerated plants' leaves as the template. During the course of these transformations, it was found that it was not possible to regenerate plants from cells transformed with vector 130020, containing the GRMZM2G143718 coding sequence driven by the ZmUbi promoter and 5'UTR. This suggested that the high-level constitutive gene expression that is expected to result from this promoter was detrimental to the plant cells during the tissue culture process. In contrast, plants could be regenerated from *B. distachyon* cells transformed with the 130028, 130036, and 130044 vectors.

Transgenic *B. distachyon* plants transformed with the 130028, 130036, and 130044 vectors were cultivated and grown to maturity. These plants were allowed to self-pollinate to produce seeds and these seeds were harvested and planted to grow T1-generation plants. T1-generation plants were grown along with wild-type *B. distachyon* plants in growth chambers with a 20 hour light/4 hour dark cycle. Plants were grown in individual pots. Variability in growth was observed among the individual events transformed with a given construct. Biomass yield data for selected events from these three constructs are shown in Table 2 along with similar data for wild-type *B. distachyon* plants.

TABLE 2

T1-generation biomass and seed data from GRMZM2G143718 *B. distachyon* plants

| Construct | Event | n | Biomass yield (g) |
|---|---|---|---|
| 130028 | B5 | 13 | 5.01 ± 2.06 |
| 130036 | F9-1 | 4 | 4.66 ± 0.88 |
| 130044 | B6-1 | 10 | 4.98 ± 1.21 |
| Wild-type | n/a | 56 | 1.70 ± 0.85 |

RNA was extracted from the leaves of 130028 *B. distachyon* plants. Quantitative RT-PCR experiments were performed, and it was found that the GRMZM2G143718 transcript was present at approximately 0.252-fold higher levels than transcript levels for the constitutively expressed native Ubi10 gene present in *B. distachyon*.

Example 2

GRMZM2G117497 Expression in *Brachypodium distachyon*

The GRMZM2G117497 coding sequence was codon-optimized for expression in *Brachypodium distachyon* (SEQ ID NO: 3). The resulting coding sequence was cloned into four separate binary vectors, each with a different promoter and 5'UTR. These binary vectors are described in Table 3.

TABLE 3

GRMZM2G117497 Constructs

| Construct Number | Promoter and 5'UTR | Coding Sequence |
|---|---|---|
| 130016 | ZmUbi (SEQ ID NO: 52) | GRMZM2G117497 (SEQ ID NO: 3) |
| 130024 | 4xRGCGR (SEQ ID NO: 19) | GRMZM2G117497 (SEQ ID NO: 3) |
| 130032 | ZmCA1 (SEQ ID NO: 18) | GRMZM2G117497 (SEQ ID NO: 3) |
| 130040 | ZmPepC (SEQ ID NO: 17) | GRMZM2G117497 (SEQ ID NO: 3) |

The vectors described in Table 3 were used to transform *B. distachyon* cells. Transformed *B. distachyon* cells were regenerated using plant tissue culture techniques to produce transgenic *B. distachyon* plants containing the GRMZM2G117497 transgene cassette in these vectors. Introduction of the transgene cassette was confirmed by PCR using DNA extracted from the regenerated plants' leaves as the template. Introduction of the transgene cassettes were confirmed by PCR using DNA extracted from the regenerated plants' leaves as the template.

T0-generation plants containing the GRMZM2G117497 gene were grown to maturity and allowed to self-pollinate to produce T1-generation seeds. The resulting T1-generation seeds were planted, with the T1-generation plants cultivated alongside wild-type *B. distachyon* plants under a 20 hour light/4 hour dark photoperiod. Plants were grown in individual pots. Biomass yield data for selected events from constructs 130032 and 130040 are shown in Table 4 along with similar data for wild-type *B. distachyon* plants.

TABLE 4

T1-generation biomass and seed data from
GRMZM2G117497 *B. distachyon* plants

| Construct | Event | n | Biomass yield (g) |
|---|---|---|---|
| 130032 | E14-2 | 4 | 2.17 ± 0.66 |
| 130040 | I4-3 | 2 | 4.61 ± 0.31 |
| Wild-type | n/a | 56 | 1.70 ± 0.85 |

Example 3

GRMZM2G158117 Expression in *Brachypodium distachyon*

The GRMZM2G158117 coding sequence was codon-optimized for expression in *Brachypodium distachyon* (SEQ ID NO: 5). The resulting coding sequence was cloned into four separate binary vectors, each with a different promoter and 5'UTR. These binary vectors are described in Table 5.

TABLE 5

GRMZM2G158117 Constructs

| Construct Number | Promoter and 5'UTR | Coding Sequence |
|---|---|---|
| 130018 | ZmUbi (SEQ ID NO: 52) | GRMZM2G158117 (SEQ ID NO: 5) |
| 130026 | 4xRGCGR (SEQ ID NO: 19) | GRMZM2G158117 (SEQ ID NO: 5) |
| 130034 | ZmCA1 (SEQ ID NO: 18) | GRMZM2G158117 (SEQ ID NO: 5) |
| 130042 | ZmPepC (SEQ ID NO: 17) | GRMZM2G158117 (SEQ ID NO: 5) |

The vectors described in Table 5 were used to transform *B. distachyon* cells. Transformed *B. distachyon* cells were regenerated using plant tissue culture techniques to produce transgenic *B. distachyon* plants containing the GRMZM2G158117 transgene cassettes. Transformation attempts with the 130018 constructs were all unsuccessful, while the other three constructs listed in Table 5 all produced transgenic plants. This suggests that the strong, constitutive expression from the ZmUbi promoter in construct 130018 produced a detrimental phenotype. Introduction of the transgene cassette was confirmed by PCR using DNA extracted from the regenerated plants' leaves as the template.

T0-generation plants were grown to maturity and self-pollinate in order to produce T1-generation seeds. The resulting T1-generation seeds were planted alongside wild-type *B. distachyon* plants of the same age under a 20 hour light/4 hour dark photoperiod. Plants were grown in individual pots. Biomass yield data for selected events from constructs 130026 and 130034 are shown in Table 6 along with similar data for wild-type *B. distachyon* plants.

TABLE 6

T1-generation biomass and seed data from
GRMZM2G158117 *B. distachyon* plants

| Construct | Event | n | Biomass yield (g) |
|---|---|---|---|
| 130026 | D5-1 | 4 | 5.75 ± 0.76 |
| 130026 | C5-1 | 4 | 5.23 ± 0.66 |
| 130026 | C5-3 | 4 | 5.51 ± 0.39 |
| 130034 | E8-2 | 8 | 4.53 ± 2.26 |
| 130034 | E8-3 | 4 | 4.68 ± 0.73 |
| 130034 | D9-1 | 5 | 4.82 ± 0.64 |
| Wild-type | n/a | 56 | 1.70 ± 0.85 |

Unexpectedly, expression of the GRMZM2G158117 open reading frame in *B. distachyon* when driven by the maize PepC promoter and 5'UTR (SEQ ID NO: 17) resulted in a detrimental phenotype. In vector 130042, the maize PepC promoter and 5'UTR are located immediately upstream of the GRMZM158117 coding sequence (SEQ ID NO: 5). In these 130042 plants, the T0-generation plants either did not survive after transplantation to soil or grew poorly and did not produce any seed. Many of these 130042 plants failed to produce any flowers.

RNA was extracted from the leaves of 130026 and 130034 *B. distachyon* plants. Quantitative RT-PCR experiments were performed, and it was found that the GRMZM2G158117 transcript was present at approximately 0.027-fold and 0.072-fold higher levels, respectively, than transcript levels for the constitutively expressed native Ubi10 gene present in *B. distachyon*.

Example 4

GRMZM2G150260 Expression in *Brachypodium distachyon*

The GRMZM2G150260 coding sequence was codon-optimized for expression in *Brachypodium distachyon* (SEQ ID NO: 7). The resulting coding sequence was cloned into three separate binary vectors, each with a different promoter and 5'UTR. These binary vectors are described in Table 7.

TABLE 7

GRMZM2G150260 Constructs

| Construct Number | Promoter and 5'UTR | Coding Sequence |
|---|---|---|
| 130019 | ZmUbi (SEQ ID NO: 52) | GRMZM2G150260 (SEQ ID NO: 7) |
| 130027 | 4xRGCGR (SEQ ID NO: 19) | GRMZM2G150260 (SEQ ID NO: 7) |
| 130035 | ZmCA1 (SEQ ID NO: 18) | GRMZM2G150260 (SEQ ID NO: 7) |

Transformed *B. distachyon* cells were regenerated using plant tissue culture techniques to produce transgenic *B. distachyon* plants containing the GRMZM2G150260 transgene cassettes described in Table 7. Introduction of the transgene cassette was confirmed by PCR using DNA extracted from the regenerated plants' leaves as the template.

T0-generation plants were grown to maturity and self-pollinate in order to produce T1-generation seeds. The resulting T1-generation seeds were planted alongside wild-type *B. distachyon* plants of the same age under a 20 hour light/4 hour dark photoperiod. Plants were grown in individual pots. Biomass yield data for selected events from these constructs are shown in Table 8 along with similar data for wild-type *B. distachyon* plants and, where available, null segregant plants.

TABLE 8

T1-generation biomass and seed data from GRMZM2G150260 *B. distachyon* plants

| Construct | Event | n | Biomass yield (g) |
|---|---|---|---|
| 130019 | B5-1 | 2 | 3.50 ± 0.66 |
| 130019 | B5-1 null segregants | 3 | 1.60 ± 0.17 |
| 130027 | B6 | 8 | 4.61 ± 1.98 |
| 130027 | E4-2 | 5 | 3.57 ± 0.75 |
| Wild-type | n/a | 56 | 1.70 ± 0.85 |

RNA was extracted from the leaves of 130027 *B. distachyon* plants. Quantitative RT-PCR experiments were performed, and it was found that the GRMZM2G150260 transcript was present at approximately 0.006-fold higher levels than transcript levels for the constitutively expressed native Ubi10 gene present in *B. distachyon*.

Example 5

GRMZM2G165042 Expression in *Brachypodium distachyon*

The GRMZM2G165042 coding sequence was codon-optimized for expression in *Brachypodium distachyon* (SEQ ID NO: 9). The resulting coding sequence was cloned into four separate binary vectors, each with a different promoter and 5'UTR. These binary vectors are described in Table 9.

TABLE 9

GRMZM2G165042 Constructs

| Construct Number | Promoter and 5'UTR | Coding Sequence |
|---|---|---|
| 130017 | ZmUbi (SEQ ID NO: 52) | GRMZM2G165042 (SEQ ID NO: 9) |
| 130025 | 4xRGCGR (SEQ ID NO: 19) | GRMZM2G165042 (SEQ ID NO: 9) |
| 130033 | ZmCA1 (SEQ ID NO: 18) | GRMZM2G165042 (SEQ ID NO: 9) |
| 130041 | ZmPepC (SEQ ID NO: 17) | GRMZM2G165042 (SEQ ID NO: 9) |

Transformed *B. distachyon* cells were regenerated using plant tissue culture techniques to produce transgenic *B. distachyon* plants containing the GRMZM2G165042 transgene cassettes described in Table 9. Introduction of the transgene cassette was confirmed by PCR using DNA extracted from the regenerated plants' leaves as the template. Transgenic plants containing the GRMZM2G165042 transgenes were grown and allowed to self-pollinate to produce T1 seed. Transgenic 130041 *B. distachyon* plants showed a detrimental growth phenotype. Eleven out of twenty-four of the 130041 plants produced did not survive following transplantation to soil. Eight of the twenty-four 130041 plants showed very poor growth, with low biomass accumulation. Five of the twenty-four 130041 plants showed good growth, but had brown lesions on their leaves. T1-generation plants from constructs 130017, 130025, and 130033 were grown in a 20 hour light/4 hour dark photoperiod in a growth chamber along with wild-type *B. distachyon* plants. Plants were grown in individual pots. Biomass yield data for selected events from these constructs are shown in Table 10 along with similar data for wild-type *B. distachyon* plants.

TABLE 10

T1-generation biomass and seed data from GRMZM2G165042 *B. distachyon* plants

| Construct | Event | n | Biomass yield (g) |
|---|---|---|---|
| 130017 | C3-2 | 2 | 1.50 ± 0.58 |
| 130033 | C1 | 3 | 2.41 ± 0.85 |
| 130033 | D7 | 4 | 1.54 ± 0.43 |
| Wild-type | n/a | 56 | 1.70 ± 0.85 |

Example 6

GRMZM2G162749 Expression in *Brachypodium distachyon*

The GRMZM2G162749 coding sequence was codon-optimized for expression in *Brachypodium distachyon* (SEQ ID NO: 11). The resulting coding sequence was cloned into four separate binary vectors, each with a different promoter and 5'UTR. These binary vectors are described in Table 11.

TABLE 11

GRMZM2G162749 Constructs

| Construct Number | Promoter and 5'UTR | Coding Sequence |
|---|---|---|
| 130021 | ZmUbi (SEQ ID NO: 52) | GRMZM2G162749 (SEQ ID NO: 11) |
| 130029 | 4xRGCGR (SEQ ID NO: 19) | GRMZM2G162749 (SEQ ID NO: 11) |
| 130037 | ZmCA1 (SEQ ID NO: 18) | GRMZM2G162749 (SEQ ID NO: 11) |
| 130045 | ZmPepC (SEQ ID NO: 17) | GRMZM2G162749 (SEQ ID NO: 11) |

Transformed *B. distachyon* cells were regenerated using plant tissue culture techniques to produce transgenic *B. distachyon* plants containing the GRMZM2G162749 transgene cassettes described in Table 11. Introduction of the transgene cassette was confirmed by PCR using DNA extracted from the regenerated plants' leaves as the template. After repeated attempts at transformation using the 130021 construct in which the ZmUbi promoter drives the GRMZM2G162749 sequence, it was not possible to generate any transgenic events. This strongly suggested that the strong constitutive expression conferred by the ZmUbi promoter was detrimental to plant regeneration. Transgenic plants were recovered from the 130029, 130037, and 130045 vectors. These plants were grown to maturity and allowed to self-pollinate to produce T1-generation seeds.

T1-generation seeds were planted and the resulting plants were grown along with wild-type *B. distachyon* plants under a 20 hour light/4 hour dark photoperiod. Plants were grown in individual pots. Biomass yield data for selected events from these constructs are shown in Table 12 along with similar data for wild-type *B. distachyon* plants.

TABLE 12

T1-generation biomass and seed data from GRMZM2G162749 *B. distachyon* plants

| Construct | Event | n | Biomass yield (g) |
|---|---|---|---|
| 130037 | B5 | 4 | 3.77 ± 0.97 |
| 130037 | D1-3 | 5 | 4.64 ± 0.82 |
| Wild-type | n/a | 56 | 1.70 ± 0.85 |

RNA was extracted from the leaves of 130037 *B. distachyon* plants. Quantitative RT-PCR experiments were performed, and it was found that the GRMZM2G162749 transcript was present at approximately 0.260-fold higher levels than transcript levels for the constitutively expressed native Ubi10 gene present in *B. distachyon*.

Example 7

Manipulating the Expression of a Native Plant Transcription Factor for Improved Growth The maize TFs listed in Table 15 were cloned into plant transformation vectors for expression in transgenic plants. It will be expected by one skilled in the art that manipulation of the expression of the native maize TFs in maize may result in increased growth, biomass accumulation, seed yield, and/or other improved plant characteristics including but not limited to drought tolerance, heat stress tolerance, and ability to withstand salt stress. It will also be well-understood by one skilled in the art that expression of orthologs of these TFs in a plant species of interest may also result in improved plant characteristics including but not limited to improved growth, biomass accumulation, seed yield, and/or resistance to biotic or abiotic stresses. Because of the expectation that altering the expression levels and/or expression profiles of orthologs of the maize TFs listed in Table 15 may improve plant characteristics, orthologs of these TFs are identified in a plant species of interest. The expression levels and/or expression profiles of the identified orthologs are then manipulated in the plant species of interest in order to improve the agronomic properties of said plants. For example, the rice (*O. sativa*) and *B. distachyon* orthologs of the maize TFs described herein are shown in Table 15.

TABLE 15

Maize TFs along with their orthologs in rice (*Oryza sativa*) and *Brachypodium distachyon*

| Maize Gene Identifier | *O. sativa* Ortholog | *B. distachyon* Ortholog |
|---|---|---|
| GRMZM2G117497 (SEQ ID NO: 4) | LOC_Os05g49240 (SEQ ID NO: 21) | Bradi2g16120 (SEQ ID NO: 37) |
| GRMZM2G143718 (SEQ ID NO: 2) | LOC_Os09g35880 (SEQ ID NO: 23) | Bradi4g35950 (SEQ ID NO: 39) |
| GRMZM2G158117 (SEQ ID NO: 6) | LOC_Os05g49240 (SEQ ID NO: 21) | Bradi2g16120 (SEQ ID NO: 37) |
| GRMZM2G150260 (SEQ ID NO: 8) | LOC_Os01g44390 (SEQ ID NO: 27) | Bradi2g44520 (SEQ ID NO: 43) |
| GRMZM2G165042 (SEQ ID NO: 10) | LOC_Os03g43810 (SEQ ID NO: 29) | Bradi1g13980 (SEQ ID NO: 45) |
| GRMZM2G162749 (SEQ ID NO: 12) | LOC_Os03g07360 (SEQ ID NO: 31) | Bradi1g73710 (SEQ ID NO: 47) |
| GRMZM2G134545 (SEQ ID NO: 14) | LOC_Os07g32510 (SEQ ID NO: 33) | Bradi1g26570 (SEQ ID NO: 49) |
| GRMZM2G077147 (SEQ ID NO: 16) | LOC_Os03g51110 (SEQ ID NO: 35) | Bradi1g10470 (SEQ ID NO: 51) |

In addition to the rice (*Oryza sativa*) and *Brachypodium distachyon* orthologs of the maize TFs listed in Table 15, further orthologs are identified through the use of bioinformatic tools. Methods for the identification of orthologous genes have been described in the scientific literature and may be used to identify TFs that are orthologous to the TFs listed in Table 15 (Li et al (2003) *Genome Res* 13:2178-2189, Fulton et al (2002) *Plant Cell* 14:1457-1467). The expression of such orthologous genes is altered in a plant of interest in order to effect a desired increase in plant growth or yield or an increased resistance to a biotic or abiotic stress.

Example 8

Determining TF Binding Sites

The binding sequences of TFs of interest are determined through a yeast one-hybrid assay approach. In this approach, the TFs listed in Table 15 are cloned into a vector suitable for protein production in a microbial system (e.g., a pET-series vector; Life Technologies). The TFs are produced in a suitable microbe harboring the protein production plasmid and purified. The purified TFs are screened against a synthetic promoter library in yeast one-hybrid assays. This promoter library contains all 8-mer DNA sequences in at least two different contexts. The results of these yeast one-hybrid assays are the binding sites for the TF being tested. Similar strategies have been described in the scientific literature for the determination of TF binding sites based on yeast one-hybrid assay screening (Pruneda-Paz et al (2009) *Science* 323:481-485).

Example 9

TF Expression in *Setaria viridis* and in Rice (*Oryza sativa*)

The constructs listed in Table 16 were used for transformation of *S. viridis* tissue. Following co-cultivation of *S. viridis* callus tissue with *A. tumefaciens* cells harboring the transformation constructs indicated in Table 16, the *S. viridis* cells were transferred to tissue culture medium for regeneration of plants. The presence of the gene of interest was confirmed using a PCR assay to detect the presence or absence of said genes. The primary transformants resulting from these transformations were grown to maturity and allowed to self-pollinate in order to produce T1-generation seeds.

TABLE 16

Constructs used for *S. viridis* transformation

| Construct | Promoter and 5'UTR | Coding Sequence |
|---|---|---|
| 130016 | ZmUbi (SEQ ID NO: 52) | GRMZM2G117497 (SEQ ID NO: 3) |
| 130018 | ZmUbi (SEQ ID NO: 52) | GRMZM2G158117 (SEQ ID NO: 5) |
| 130019 | ZmUbi (SEQ ID NO: 52) | GRMZM2G150260 (SEQ ID NO: 7) |
| 130020 | ZmUbi (SEQ ID NO: 52) | GRMZM2G143718 (SEQ ID NO: 1) |
| 130021 | ZmUbi (SEQ ID NO: 52) | GRMZM2G162749 (SEQ ID NO: 11) |
| 130024 | 4xRGCGR (SEQ ID NO: 19) | GRMZM2G117497 (SEQ ID NO: 3) |
| 130026 | 4xRGCGR (SEQ ID NO: 19) | GRMZM2G158117 (SEQ ID NO: 5) |
| 130027 | 4xRGCGR (SEQ ID NO: 19) | GRMZM2G150260 (SEQ ID NO: 7) |
| 130028 | 4xRGCGR (SEQ ID NO: 19) | GRMZM2G143718 (SEQ ID NO: 1) |
| 130029 | 4xRGCGR (SEQ ID NO: 19) | GRMZM2G162749 (SEQ ID NO: 11) |
| 130032 | ZmCA1 (SEQ ID NO: 18) | GRMZM2G117497 (SEQ ID NO: 3) |
| 130034 | ZmCA1 (SEQ ID NO: 18) | GRMZM2G158117 (SEQ ID NO: 5) |
| 130035 | ZmCA1 (SEQ ID NO: 18) | GRMZM2G150260 (SEQ ID NO: 7) |
| 130036 | ZmCA1 (SEQ ID NO: 18) | GRMZM2G143718 (SEQ ID NO: 1) |
| 130037 | ZmCA1 (SEQ ID NO: 18) | GRMZM2G162749 (SEQ ID NO: 11) |
| 130040 | ZmPepC (SEQ ID NO: 17) | GRMZM2G117497 (SEQ ID NO: 3) |
| 130042 | ZmPepC (SEQ ID NO: 17) | GRMZM2G158117 (SEQ ID NO: 5) |
| 130043 | ZmPepC (SEQ ID NO: 17) | GRMZM2G150260 (SEQ ID NO: 7) |
| 130044 | ZmPepC (SEQ ID NO: 17) | GRMZM2G143718 (SEQ ID NO: 1) |
| 130045 | ZmPepC (SEQ ID NO: 17) | GRMZM2G162749 (SEQ ID NO: 11) |

T1-generation seeds of *S. viridis* plants transformed with the constructs listed in Table 16 were planted in soil and the resulting T1 plants were grown in a greenhouse in individual pots along with wild-type *S. viridis* plants. Table 17 shows the dry weight of the harvested biomass from the available *S. viridis* lines transformed with vectors 130027 and 130044 along with the biomass of wild-type *S. viridis* plants grown alongside these 130027 and 130044 plants.

TABLE 17

Dry weight of selected 130027 and 130044 *S. viridis* events

| | Dry Weight (g) |
|---|---|
| 130027.05a | 8.42 ± 2.19 |
| 130027.06a | 9.64 ± 1.64 |
| 130027.06b | 8.18 ± 2.03 |
| 130027.07b | 9.02 ± 1.79 |
| 130027.10 | 7.72 ± 2.44 |
| 130027.11a | 8.39 ± 1.47 |
| 130044.03 | 10.25 ± 1.25 |
| WT | 8.13 ± 1.95 |

Table 18 shows the dry weight of the harvested biomass from the available *S. viridis* lines transformed with vectors 130026, 130034, 130037, and 130045 along with the biomass of wild-type *S. viridis* plants grown alongside these plants.

TABLE 18

Dry weight of selected 130026, 130034, 130037, and 130045 *S. viridis* events

| Event | Dry Weight (g) |
|---|---|
| 130026.01 | 8.39 ± 2.88 |
| 130026.02 | 11.04 ± 2.2 |
| 130026.04a | 9.1 ± 2.8 |
| 130026.04b | 9.74 ± 2.61 |
| 130034.06a | 9.25 ± 2.2 |
| 130034.11a | 9.04 ± 2.74 |
| 130034.11b | 9.88 ± 1.54 |
| 130034.11c | 9.63 ± 2.27 |
| 130034.12 | 9.14 ± 2.29 |
| 130034.18a | 8.46 ± 1.67 |
| 130034.18b | 5.49 ± 1.49 |
| 130037.09 | 8.73 ± 3.26 |
| 130037.11 | 10.58 ± 0.78 |
| 130037.12 | 7.51 ± 2.97 |
| 130037.13 | 5.15 ± 3.39 |
| 130037.16 | 4.7 ± 2.53 |
| 130037.17 | 8.68 ± 1.82 |
| 130045.03a | 8.65 ± 1.75 |
| WT | 8.18 ± 2.96 |

The constructs listed in Table 16 were also used to transform cells of rice (*Oryza sativa* cv. *Kitaake*). Following co-cultivation with *A. tumefaciens* cells harboring the transformation constructs described in Table 16, the transformed rice cells were regenerated using tissue culture techniques to produce transgenic plants. The presence of the genes of interest in the regenerated rice plants was confirmed by PCR using DNA extracted from the plants' leaves and primers specific to the genes of interest. The primary transformants resulting from these transformations were grown to maturity and allowed to self-pollinate in order to produce T1-generation seeds. Following the harvest of T1-generation seeds, these seeds are planted in soil and allowed to germinate along with wild-type and/or null segregant plants as negative controls. The T1-generation plants are genotyped by PCR or another appropriate molecular assay in order to detect the presence or absence of the TF gene of interest. T1 plants are allowed to grow to maturity and self-pollinate to produce T2-generation seeds. The total above-ground biomass is harvested and dried in a 37° C. oven. Separately, the seeds are harvested, dried, and weighed, and are counted. The dry weight of the biomass produced by rice plants transformed with one of the constructs listed in Table 16 is compared with the dry weight of the biomass produced by wild-type and/or null segregant rice plants. The total number and dry weight of the seeds produced by rice plants transformed with one of the constructs listed in Table 16 is also compared with the dry weight and total number of seeds produced by wild-type and/or null segregant rice plants. Appropriate statistical analyses are performed in order to determine whether the transgenic rice plants produce significantly more biomass and/or seed than the negative control plants.

Example 10

Testing Salt and High-pH Tolerance

As described in Example 11, the vectors listed in Table 16 were used to transform rice (*Oryza sativa* cv. *Kitaake*). The resulting rice plants were grown in a greenhouse setting. These rice plants were challenged with water as described in Table 19. This Table shows the average concentrations of the various ions listed during the time the rice plants were cultivated as well as the average pH over this time period. The high pH, high $Na^+$, high S, high $SO_4^{2-}$, and high $Cl^-$ contents in this water are significantly outside the range that is typically used to water plants.

TABLE 19

Ion content of water used with TF-expressing rice plants

|  | Average value (pH or ppm) |
|---|---|
| pH | 9.57 |
| N as $NH_4^+$ | 0.16 |
| N as $NO3^-$ | 1.83 |
| $Ca^{2+}$ | 28.19 |
| $Mg^{2+}$ | 23.49 |
| $Na^+$ | 59.72 |
| $K^+$ | 5.36 |
| S | 51.48 |
| $SO_4^{2-}$ | 154.25 |
| P | 0.50 |
| $Cl^-$ | 22.90 |
| $CO_3^{2-}$ | 14.41 |
| $HCO_3^-$ | 65.90 |

All rice plants transformed with the vectors listed in Table 16 appeared phenotypically normal during vegetative growth. On reaching reproductive stage, however, many of the plants were unable to produce viable seeds. Table 20 summarizes the seed production of the rice plants transformed with the vectors described in Table 16.

TABLE 20

Seed production by transgenic rice plants

| Construct | Number of Events | Events with Viable Seed |
|---|---|---|
| 130018 | 5 | 0 |
| 130020 | 11 | 0 |
| 130021 | 8 | 0 |
| 130024 | 21 | 16 |
| 130026 | 21 | 9 |
| 130027 | 32 | 0 |
| 130028 | 31 | 3 |
| 130029 | 12 | 0 |
| 130032 | 41 | 0 |
| 130035 | 2 | 0 |
| 130036 | 2 | 0 |
| 130037 | 5 | 0 |
| 130040 | 1 | 0 |
| 130042 | 14 | 0 |
| 130044 | 15 | 0 |

As shown in Table 20, most of these transgenic rice lines were unable to produce viable seed when challenged with the water described in Table 19. Exceptions were transgenic rice lines transformed with the 130024, 130026, and 130028 constructs. Many of these plants successfully self-pollinated and produced viable seeds.

Seeds produced by rice plants expressing the TF of interest were planted in soil in order to cultivate T1-generation rice. T1-generation rice plants are grown under normal conditions as well as under high-salt and/or high-pH conditions along with null segregant and/or wild-type negative control plants. Following maturation, the plants are allowed to self-pollinate to produce seeds. The biomass produced by the rice plants is harvested along with the seeds and is dried. The weight of the biomass produced, the number of seeds produced, and the weight of the seeds produced by the rice plants are measured and appropriate statistical analyses are performed in order to compare biomass and seed production by TF-expressing rice plants with biomass and seed production by negative control plants.

We claim:

1. A method of increasing terminal biomass in a plant, said method comprising transforming a plant with at least one expression construct comprising a promoter sequence comprising SEQ ID NO: 19 operably linked to a nucleotide sequence encoding a transcription factor polypeptide that shares at least 95% identity with SEQ ID NO: 2, regenerating the transformed plant, and selecting a transformed plant that exhibits increased terminal biomass relative to a control plant.

2. The method of claim 1, wherein said plant of interest is a monocotyledonous plant.

3. The method of claim 1, wherein said plant of interest is a dicotyledonous plant.

4. An expression construct comprising a promoter selected from the group consisting of SEQ ID NOs: 17, 18, and 19 operably linked to a nucleotide sequence encoding a transcription factor polypeptide that shares at least 95% identity with SEQ ID NO: 2, wherein said transcription factor polypeptide has transcription factor activity.

5. A plant stably transformed with the expression construct of claim 4 wherein said plant exhibits increased terminal biomass relative to a control plant.

6. A seed comprising an expression construct comprising a promoter sequence comprising SEQ ID NO: 17 operably linked to a nucleotide sequence encoding a transcription factor polypeptide that shares at least 95% identity with SEQ ID NO: 2.

7. The method of claim 1 wherein the transformed plant exhibits increased seed yield.

8. The plant of claim 5 wherein said promoter comprises the nucleic acid sequence of SEQ ID NO: 19, and wherein the transformed plant exhibits increased seed yield.

* * * * *

UNITED STATES PATENT AND TRADEMARK OFFICE
CERTIFICATE OF CORRECTION

PATENT NO. : 11,060,101 B2
APPLICATION NO. : 15/324501
DATED : July 13, 2021
INVENTOR(S) : Thomas P. Brutnell et al.

It is certified that error appears in the above-identified patent and that said Letters Patent is hereby corrected as shown below:

On the Title Page

At Column 2, under the heading "Other Publications", the text at Line 13, "transgneic" should be changed to -- transgenic --.

At Column 2, under the heading "Other Publications", the text at Line 21, "B-boxzinc" should be changed to -- B-box zinc --.

In the Claims

At Column 94, Claim 6, Line 39, the text "SEQ ID NO: 17" should be changed to -- SEQ ID NO: 19 --.

Signed and Sealed this
Nineteenth Day of July, 2022

Katherine Kelly Vidal
*Director of the United States Patent and Trademark Office*